(12) United States Patent
Clemente et al.

(10) Patent No.: US 9,802,030 B2
(45) Date of Patent: Oct. 31, 2017

(54) INTEGRATED SLIDING SEAL FLUID PATHWAY CONNECTION AND DRUG CONTAINERS FOR DRUG DELIVERY PUMPS

(71) Applicant: UNL Holdings LLC, New York, NY (US)

(72) Inventors: Matthew J. Clemente, Downingtown, PA (US); Ian B. Hanson, Wayne, PA (US); Paul F. Bente, IV, Wayne, PA (US); Ryan M. Agard, Royersford, PA (US); Nicholas J. Ciccarelli, Philadelphia, PA (US)

(73) Assignee: UNL Holdings LLC, New York, NY (US)

( * ) Notice: Subject to any disclaimer, the term of this patent is extended or adjusted under 35 U.S.C. 154(b) by 805 days.

(21) Appl. No.: 13/796,156

(22) Filed: Mar. 12, 2013

(65) Prior Publication Data
US 2014/0213975 A1    Jul. 31, 2014

Related U.S. Application Data

(60) Provisional application No. 61/756,638, filed on Jan. 25, 2013.

(51) Int. Cl.
*A61M 39/04* (2006.01)
*A61M 5/145* (2006.01)
(Continued)

(52) U.S. Cl.
CPC .......... *A61M 39/04* (2013.01); *A61M 5/1452* (2013.01); *A61M 5/14248* (2013.01);
(Continued)

(58) Field of Classification Search
CPC .. A61M 5/14248; A61M 39/04; A61M 39/18; A61M 5/1452; A61M 5/158; A61M 5/3157
(Continued)

(56) References Cited

U.S. PATENT DOCUMENTS 3,336,924 A    8/1967  Sarnoff et al.
3,401,692 A *  9/1968  Harris, Jr. ......... A61M 5/31531
                                                    141/330
(Continued)

FOREIGN PATENT DOCUMENTS

CN    101557847 A    10/2009
CN    101631585 A    1/2010
(Continued)

OTHER PUBLICATIONS

European Patent Office, Communication Relating to the Results of the Partial International Search in International Application No. PCT/US2012/053241, 2 pages (Nov. 30, 2012).
(Continued)

*Primary Examiner* — Bhisma Mehta
*Assistant Examiner* — Hamza Darb
(74) *Attorney, Agent, or Firm* — Hamilton, Brook, Smith & Reynolds, P.C.

(57) ABSTRACT

A fluid pathway connection includes a piercing member, a connection hub, and a sliding pierceable seal, wherein the sliding pierceable seal is configured to move from a first position, where the piercing member is initially retained within a sterile cavity between the connection hub and the sliding pierceable seal, to a second position, where the pierceable seal has been penetrated by the piercing member. A filter may be utilized to enclose the sterile cavity from the outside environment. The fluid pathway connection may further be configured to move to a third position where one
(Continued)

or more interconnects and/or one or more corresponding contacts are permitted to transmit a signal to the user. Such fluid pathway connections may be integrated into a drug container having a barrel and a plunger seal. A drug delivery pump includes such integrated fluid pathway connections and drug containers.

21 Claims, 10 Drawing Sheets

(51) Int. Cl.
  *A61M 5/158* (2006.01)
  *A61M 39/18* (2006.01)
  *A61M 5/142* (2006.01)
  *A61M 5/315* (2006.01)
(52) U.S. Cl.
  CPC ............ *A61M 5/158* (2013.01); *A61M 39/18* (2013.01); *A61M 5/3157* (2013.01)
(58) Field of Classification Search
  USPC .................. 604/131–135, 143, 148, 151–155
  See application file for complete search history.

(56)           References Cited

U.S. PATENT DOCUMENTS

| | | |
|---|---|---|
| 3,413,974 A | 12/1968 | Cohen |
| 3,940,003 A | 2/1976 | Larson |
| 4,004,586 A | 1/1977 | Christensen et al. |
| 4,048,997 A | 9/1977 | Raghavachari et al. |
| 4,565,543 A | 1/1986 | Bekkering et al. |
| 4,673,400 A | 6/1987 | Martin |
| 4,685,903 A | 8/1987 | Cable et al. |
| 4,755,173 A | 7/1988 | Konopka et al. |
| 4,840,620 A | 6/1989 | Kobayashi et al. |
| 5,147,311 A * | 9/1992 | Pickhard ............... A61M 5/148 604/131 |
| 5,167,816 A | 12/1992 | Kruger et al. |
| 5,795,339 A | 8/1998 | Erskine |
| 5,851,197 A | 12/1998 | Marano et al. |
| 5,858,001 A | 1/1999 | Tsals et al. |
| 6,248,093 B1 | 6/2001 | Moberg |
| 6,368,314 B1 | 4/2002 | Kipfer et al. |
| 6,699,218 B2 | 3/2004 | Flaherty et al. |
| 7,063,684 B2 | 6/2006 | Moberg |
| 7,250,037 B2 | 7/2007 | Shermer et al. |
| D564,087 S | 3/2008 | Yodfat et al. |
| D585,543 S | 1/2009 | Yodfat et al. |
| 7,479,135 B2 | 1/2009 | Richter et al. |
| 7,611,503 B2 | 11/2009 | Spohn et al. |
| 7,780,636 B2 | 8/2010 | Radmer et al. |
| 7,803,134 B2 | 9/2010 | Sharifi et al. |
| 7,846,132 B2 | 12/2010 | Gravesen et al. |
| 7,879,010 B2 | 2/2011 | Hunn et al. |
| 7,905,859 B2 | 3/2011 | Bynum et al. |
| 7,927,306 B2 | 4/2011 | Cross et al. |
| 7,967,795 B1 | 6/2011 | Cabiri |
| 8,029,472 B2 | 10/2011 | Leinsing et al. |
| 8,048,031 B2 | 11/2011 | Shaw et al. |
| 8,152,771 B2 | 4/2012 | Mogensen et al. |
| 8,157,769 B2 | 4/2012 | Cabiri |
| 8,162,892 B2 | 4/2012 | Mogensen et al. |
| 8,167,844 B2 | 5/2012 | Dillard, III |
| 8,187,232 B2 | 5/2012 | Chong et al. |
| D669,165 S | 10/2012 | Estes et al. |
| 8,409,145 B2 | 4/2013 | Raymond et al. |
| D684,685 S | 6/2013 | Schneider et al. |
| D684,686 S | 6/2013 | Cronenberg |
| D685,083 S | 6/2013 | Schneider et al. |
| 8,591,465 B2 | 11/2013 | Hommann |
| D709,183 S | 7/2014 | Kemlein |
| 8,795,234 B2 | 8/2014 | Kadamus et al. |
| D723,157 S | 2/2015 | Clemente et al. |
| 9,005,169 B2 | 4/2015 | Gravesen et al. |
| D745,142 S | 12/2015 | O'Connor et al. |
| D752,442 S | 3/2016 | O'Donahue |
| 2003/0199816 A1 * | 10/2003 | Ramming ............. A61M 5/284 604/89 |
| 2004/0092878 A1 | 5/2004 | Flaherty |
| 2007/0010789 A1 | 1/2007 | Peter et al. |
| 2007/0179444 A1 | 8/2007 | Causey et al. |
| 2008/0132842 A1 | 6/2008 | Flaherty |
| 2008/0269683 A1 | 10/2008 | Bikovsky |
| 2008/0269687 A1 | 10/2008 | Chong et al. |
| 2009/0124979 A1 | 5/2009 | Raymond et al. |
| 2009/0204077 A1 | 8/2009 | Hasted et al. |
| 2009/0240240 A1 | 9/2009 | Hines et al. |
| 2011/0098652 A1 | 4/2011 | Hasted et al. |
| 2011/0160678 A1 | 6/2011 | Chong et al. |
| 2011/0166509 A1 | 7/2011 | Gross et al. |
| 2011/0270188 A1 * | 11/2011 | Caffey ............. A61M 5/14526 604/151 |
| 2012/0035546 A1 | 2/2012 | Cabiri |
| 2012/0096953 A1 | 4/2012 | Bente, IV et al. |
| 2012/0123354 A1 | 5/2012 | Woehr |
| 2012/0211946 A1 | 8/2012 | Halili et al. |
| 2013/0060196 A1 | 3/2013 | O'Connor et al. |
| 2013/0066274 A1 | 3/2013 | O'Connor et al. |
| 2013/0131595 A1 | 5/2013 | Ekman et al. |
| 2014/0238542 A1 * | 8/2014 | Kvale ................. A61J 1/1406 141/329 |

FOREIGN PATENT DOCUMENTS

| | | |
|---|---|---|
| EP | 1219283 A2 | 7/2002 |
| EP | 1702635 A2 | 9/2006 |
| EP | 1341569 B1 | 1/2007 |
| EP | 1427471 B1 | 2/2008 |
| EP | 1695727 B1 | 7/2008 |
| EP | 1513580 B1 | 3/2009 |
| EP | 2077128 A1 | 7/2009 |
| EP | 2269559 A2 | 1/2011 |
| EP | 2379134 A1 | 10/2011 |
| EP | 2429612 A1 | 3/2012 |
| EP | 2433663 A1 | 3/2012 |
| JP | 2002-524217 A | 8/2002 |
| JP | 2003-527159 A | 9/2003 |
| JP | 2004-195227 A | 7/2004 |
| JP | 2004-528939 A | 9/2004 |
| JP | 2010-501211 A | 1/2010 |
| JP | 2010-501281 A | 1/2010 |
| JP | 2010-528810 A | 8/2010 |
| JP | 2010-531196 A | 9/2010 |
| JP | 2010-538751 A | 12/2010 |
| JP | 2011-045537 A | 3/2011 |
| JP | 2011-511689 A | 4/2011 |
| WO | WO 95/19194 A1 | 7/1995 |
| WO | WO 99/48546 A1 | 9/1999 |
| WO | WO 00/15292 A2 | 3/2000 |
| WO | WO 01/30424 A1 | 5/2001 |
| WO | WO 03/024504 A2 | 3/2003 |
| WO | WO 03/103763 A1 | 12/2003 |
| WO | WO 2004/035116 A1 | 4/2004 |
| WO | WO 2004/062714 A1 | 7/2004 |
| WO | WO 2005/037350 A2 | 4/2005 |
| WO | WO 2005/044344 A1 | 5/2005 |
| WO | WO 2006/129196 A1 | 12/2006 |
| WO | WO 2008/024808 A2 | 2/2008 |
| WO | WO 2008/105954 A2 | 9/2008 |
| WO | WO 2008/133702 A1 | 11/2008 |
| WO | WO 2008/153460 A1 | 12/2008 |
| WO | WO 2009/101145 A1 | 8/2009 |
| WO | WO 2010/029054 A1 | 3/2010 |
| WO | WO 2010/077807 A1 | 7/2010 |
| WO | WO 2010/084113 A1 | 7/2010 |
| WO | WO 2010/085338 A1 | 7/2010 |
| WO | WO 2010/112377 A1 | 10/2010 |
| WO | WO 2010/132196 A1 | 11/2010 |
| WO | WO 2010/139672 A1 | 12/2010 |
| WO | WO 2011/006652 A1 | 1/2011 |
| WO | WO 2011-046950 A1 | 4/2011 |
| WO | WO 2011/090956 A2 | 7/2011 |

(56) References Cited

FOREIGN PATENT DOCUMENTS

| WO | WO 2011/121023 A1 | 10/2011 |
| WO | WO 2012/032411 A2 | 3/2012 |
| WO | WO 2012/131044 A1 | 10/2012 |
| WO | WO 2013-033467 A2 | 3/2013 |
| WO | WO 2013/156224 A1 | 10/2013 |

OTHER PUBLICATIONS

European Patent Office, International Search Report in International Application No. PCT/US2012/053174, 4 pages (Mar. 28, 2013).
European Patent Office, International Search Report in International Application No. PCT/US2012/053241, 6 pages (Feb. 28, 2013).
European Patent Office, International Search Report in International Patent Application No. PCT/US2012/054861, 8 pages,(Feb. 18, 2013).
European Patent Office, Written Opinion of the International Searching Authority in International Application No. PCT/US2012/053174, 6 pages (Mar. 28, 2013).
European Patent Office, Written Opinion of the International Searching Authority in International Application No. PCT/US2012/053241, 8 pages (Feb. 28, 2013).
Preliminary Amendment and Application Data Sheet Filed in National Phase of WO 2011/090956 A2 (U.S. Appl. No. 13/521,181) (Jul. 9, 2012).
European Patent Office, International Search Report and Written Opinion in International Patent Application No. PCT/US2013/030478, mailed Nov. 18, 2013, 11 pages.
U.S. Food and Drug Administration, "Infusion Pump Improvement Initiative," Apr. 2010, 6 pp.
Meng et al., "MEMS-enabled implantable drug infusion pumps for laboratory animal research, preclinical, and clinical applications," *Adv. Drug. Deliv. Rev.*, 64(14), Nov. 2012, pp. 1628-1638.

* cited by examiner

INTEGRATED SLIDING SEAL FLUID PATHWAY CONNECTION AND DRUG CONTAINERS FOR DRUG DELIVERY PUMPS

CROSS-REFERENCE TO RELATED APPLICATIONS

This application claims priority to U.S. Provisional Application No. 61/756,638, filed on Jan. 25, 2013, which is included by reference herein in its entirety for all purposes.

FIELD

This invention relates to drug delivery pumps. More particularly, this invention relates to fluid pathway connections which are integrated into or within drug containers, drug delivery pumps which utilize these connections, the methods of operating such devices, and the methods of assembling such devices.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injections pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

SUMMARY

The present invention provides container connections which maintain the sterility of the fluid pathway and which are integrated into the drug container, and drug delivery pumps which incorporate such sterile fluid pathway connections to drug containers, the methods of operating such devices, and the methods of assembling such devices. The fluid pathway connections of the present invention provide integrated safety features which ensure the sterility of the fluid pathway before, during, and after drug delivery. In one aspect, the fluid pathway remains disconnected from the drug container until the device has been initiated by the user. In a second aspect, the fluid pathway maintains the sterility of the piercing member prior to connection with the drug container within a sterile cavity prior to activation by the user. Upon activation by the user, the sliding pierceable seal is translated, such as by pneumatic pressure or force within the drug fluid, towards a substantially fixed piercing member such that the sliding pierceable seal is pierced and the fluid pathway is connected or opened to enable fluid flow through the fluid pathway for drug delivery into the body of the user. Accordingly, the novel devices of the present invention alleviate one or more of the problems associated with prior art devices, such as those referred to above.

A drug pump, such as an infusion pump or a bolus injector, may be needed to deliver a particular amount of drug fluid within a period of time. When delivering fluid subcutaneously it is important to control the flow of fluid that is delivered into the patient and to maintain the sterility of the drug container and fluid pathway prior to activation or operation of the drug delivery device. It may be desired that the fluid pathway connection remains disconnected, for container integrity, sterility, and other purposes, until the user has activated the device and initiated drug flow from a drug container to the patient. Some drug pump systems may utilize one or more active fluid pathway control mechanisms to prevent premature fluid pathway connection and/or drug delivery. Other drug pump systems are configured such that fluid pathway connection is made upon manufacture, and drug delivery is blocked until desired by the user. Such designs do not provide the beneficial advantages associated with maintaining container integrity and sterility of the internal components of the drug delivery device. The present invention provides an integrated fluid pathway connection mechanism for drug delivery pumps. The novel embodiments of the present invention at once provide a connection mechanism to open or connect a sterile fluid pathway between a drug container and a fluid conduit without adding unnecessary steps of use for the user. This is enabled by utilizing activation of the drive mechanism and translation of the plunger seal, and the resulting pneumatic pressure within the drug fluid, to force translation of a sliding pierceable seal. The translation of the sliding pierceable seal causes it to impact upon an initially substantially stationary or fixed piercing member to open a fluid pathway between the drug container and the fluid conduit.

Accordingly, the embodiments of the present invention provide a sterile fluid pathway connection that is integrated into a drug container and opened, connected, activated, or otherwise enabled by the operation of the device and drive mechanism. The activation of the drive mechanism and the force transferred from the drive mechanism to the plunger seal is, itself, used to open a sterile fluid pathway between the drug container and the fluid conduit. Accordingly, container integrity and sterility of the drug container may be maintained prior to and during operation of the device. This novel configuration also automates the sterile fluid pathway connection step, greatly reducing the complexity of the device and operational steps needed to be performed by the device or the user. The novel embodiments of the present invention also permit more device component configurations and reduce the layout or overall footprint of the device, since no separate sterile fluid pathway connection mechanism are needed on the cap side of the drug container. The present invention may also be fully implemented or utilized in standard drug fill-finish processes, including processes that require the pulling of a vacuum. Additionally, the present invention may also integrate a number of different status indication mechanisms into the device, including utilizing the piercing member and the plunger seal as parts of an end-of-dose indication mechanism. Such components and devices provide true end-of-dose indication coupled to the actual travel and drug delivery status of the plunger seal.

In a first embodiment, the present invention provides a fluid pathway connection which includes a piercing member, a connection hub, and a sliding pierceable seal. The piercing member is initially retained in a first position within a sterile cavity between the connection hub and the sliding pierceable seal. Upon activation by the user, the pierceable seal is caused to move to a second position where the pierceable seal is penetrated by the piercing member. Force, such as pneumatic force, applied on the sliding pierceable seal on the side opposing the sterile cavity causes translation of the sliding pierceable seal towards the piercing member. The translation of the sliding pierceable seal causes it to impact upon an initially substantially stationary or fixed piercing member to open a fluid pathway through the sliding piercing member. Accordingly, the sliding pierceable seal is configured to move from the first position to the second position by a force applied by a drug fluid on the sliding pierceable seal. Penetration by the piercing member of the sliding pierceable seal upon movement of the sliding pierceable seal from the first position to the second position opens a fluid pathway through the sliding piercing member and the piercing member to a fluid conduit.

In at least one embodiment, the pierceable seal has a seal barrier that may be penetrated by the piercing member. The piercing member may initially be in contact with, or adjacent to, the seal barrier. The fluid pathway connection may further include a seal mount attached to the sliding pierceable seal, wherein the seal mount is capable of engaging with and translating upon the connection hub and wherein the piercing member is initially in contact with, or adjacent to, the seal barrier. The piercing member may be configured to pass into the connection hub and connect to a fluid conduit. In another embodiment, the connection hub may connect the piercing member to the fluid conduit, and the fluid conduit may be at least partially a part of the connection hub.

The fluid pathway connections of the present invention may further include one or more interconnects and, optionally, one or more corresponding contacts to transmit a signal to the user. For example, the interconnect may be within or at least partially proximal to a plunger seal translatable within a drug container such that the piercing member is capable of penetrating the plunger seal and acting as a contact for the interconnect to transmit a signal to the user. Additionally or alternatively, one of either the interconnects and/or the contacts is within or at least partially proximal to a plunger seal translatable within a drug container and the other is within or at least partially distal to the sliding pierceable seal to transmit a signal to the user when the plunger seal and the sliding pierceable seal are substantially in contact. A number of known interconnects and contacts may be utilized within the embodiments of the present invention, which would readily be appreciated by an ordinarily skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes. Additionally, the fluid pathway connections may include one or more flow restrictors. In at least one embodiment, the connection hub may at least partially function as a fluid conduit and/or flow restrictor. In at least one embodiment, the fluid pathway connection further includes a filter. A number of known filters may be utilized within the embodiments of the present invention, which would readily be appreciated by an ordinarily skilled artisan. For example the filter may be a permeable membrane, semi-permeable membrane, and/or porous membrane, which encloses the sterile cavity from the outside environment.

In another embodiment, the present invention provides an integrated fluid pathway connection and drug container having a piercing member, a connection hub, and a sliding pierceable seal integrated at least partially within a drug container having a barrel and a plunger seal. The sliding pierceable seal is translatable upon a connection post of the connection hub and is configured to move from a first position, where the piercing member is initially retained within a sterile cavity between the connection hub and the sliding pierceable seal, to a second position, where the pierceable seal has been penetrated by the piercing member. The drug container contains a drug chamber between the sliding pierceable seal and the plunger seal to initially retain a drug fluid, and wherein the sliding pierceable seal is configured to move from the first position to the second position by a force applied by the drug fluid on the sliding pierceable seal. In at least one embodiment, the pierceable seal has a seal barrier that may be penetrated by the piercing member and the piercing member is initially in contact with, or adjacent to, the seal barrier.

The integrated fluid pathway connection may further include a seal mount attached to the sliding pierceable seal, wherein the seal mount slidably engages the connection hub to permit translation of the sliding pierceable seal in the distal direction but prevent translation in the proximal direction. Such a configuration may be utilized to permit the drug chamber of the drug container to be evacuated, such as by vacuum, prior to filling with a drug fluid without compromising the function of the sterile fluid pathway connection. In at least one embodiment, the connection hub has a header with a conduit port, a chamber, and a vacuum port with a channel that leads into the chamber such that the sterile cavity may be evacuated through the channel. The conduit port and may have a membrane or seal to permit fluid flow out of the chamber. Similarly, the vacuum port may be capable of being plugged, such as by a polymeric plug. Such configurations may allow, for example, the sterile cavity to be evacuated to maintain sterility, the maintenance of a pressure equilibrium between the sterile cavity and the opposing side of the sliding pierceable seal, and/or assist in maintaining the relative positions of the components prior to operation of the device by the user.

In at least one embodiment of the present invention, the sliding pierceable seal is translatable upon the connection post of the connection hub and is further configured to move from the second position, where the pierceable seal has been penetrated by the piercing member, to a third position where one or more interconnects and one or more corresponding contacts are permitted to transmit a signal to the user. In one such embodiment, one of either the interconnects and the contacts is upon an aspect of a drive mechanism and the other is within or at least partially proximal to the plunger seal to transmit a signal to the user when the plunger seal and the sliding pierceable seal are substantially in contact. Alternatively, one of either the interconnects and the contacts is within or at least partially distal to the pierceable sliding seal and the other is proximal to the connection hub to transmit a signal to the user when the plunger seal and the sliding pierceable seal are substantially in contact. A number of known interconnects and contacts may be utilized within the embodiments of the present invention, which would readily be appreciated by an ordinarily skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes. Additionally, the fluid pathway connections may include one or more flow restrictors. In at least one embodiment, the connection hub may at least partially function as a fluid conduit and/or flow restrictor. In at least one embodiment, the fluid pathway connection further includes a filter. A number of known filters may be utilized within the embodiments of the present invention, which would readily be appreciated by an ordinarily skilled artisan. For example the filter may be a permeable membrane, semi-permeable membrane, and/or porous membrane, which encloses the sterile cavity from the outside environment.

In yet another embodiment, the present invention provides a drug delivery pump with integrated sterility maintenance features comprises a housing within which an activation mechanism, an insertion mechanism, and a drug container having a plunger seal may be mounted. The drug container is connected at one end to a drive mechanism and at another end to a fluid pathway connection. The fluid pathway connection includes a piercing member, a connection hub, and a sliding pierceable seal, wherein the sliding pierceable seal is configured to move from a first position, where the piercing member is initially retained within a sterile cavity between the connection hub and the sliding pierceable seal, to a second position, where the pierceable seal has been penetrated by the piercing member. The drug container contains a drug chamber between the sliding pierceable seal and the plunger seal to initially retain a drug fluid, and wherein the sliding pierceable seal is configured to move from the first position to the second position by a force applied by the drug fluid on the sliding pierceable seal. In at least one embodiment, the pierceable seal has a seal barrier that may be penetrated by the piercing member and the piercing member is initially in contact with, or adjacent to, the seal barrier.

The drug pump may further include a seal mount attached to the sliding pierceable seal, wherein the seal mount slidably engages the connection hub to permit translation of the sliding pierceable seal in the distal direction but prevent translation in the proximal direction. Such a configuration may be utilized to permit the drug chamber of the drug container to be evacuated, such as by vacuum, prior to filling with a drug fluid without compromising the function of the sterile fluid pathway connection. In at least one embodiment, the connection hub has a header with a conduit port, a chamber, and a vacuum port with a channel that leads into the chamber such that the sterile cavity may be evacuated through the channel. The conduit port and may have a membrane or seal to permit fluid flow out of the chamber. Similarly, the vacuum port may be capable of being plugged, such as by a polymeric plug. Such configurations may allow, for example, the sterile cavity to be evacuated to maintain sterility, the maintenance of a pressure equilibrium between the sterile cavity and the opposing side of the sliding pierceable seal, and/or assist in maintaining the relative positions of the components prior to operation of the device by the user.

In at least one embodiment of the present invention, the sliding pierceable seal is translatable upon the connection post of the connection hub and is further configured to move from the second position, where the pierceable seal has been penetrated by the piercing member, to a third position where one or more interconnects and one or more corresponding contacts are permitted to transmit a signal to the user. The one or more interconnects and the one or more corresponding contacts are configured such that either: (a.) one of either the interconnects and the contacts is upon an aspect of the drive mechanism and the other is within or at least partially proximal to the plunger seal to transmit a signal to the user when the plunger seal and the sliding pierceable seal are substantially in contact; or (b.) one of either the interconnects and the contacts is within or at least partially distal to the pierceable sliding seal and the other is proximal to the connection hub to transmit a signal to the user when the plunger seal and the sliding pierceable seal are substantially in contact. A number of known interconnects and contacts may be utilized within the embodiments of the present invention, which would readily be appreciated by an ordinarily skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes. Additionally, the fluid pathway connections may include one or more flow restrictors. In at least one embodiment, the connection hub may at least partially function as a fluid conduit and/or flow restrictor. In at least one embodiment, the fluid pathway connection further includes a filter. A number of known filters may be utilized within the embodiments of the present invention, which would readily be appreciated by an ordinarily skilled artisan. For example the filter may be a permeable membrane, semi-permeable membrane, and/or porous membrane, which encloses the sterile cavity from the outside environment.

The novel devices of the present invention provide container connections which maintain the sterility of the fluid pathway and which are integrated into the drug container, and drug delivery pumps which incorporate such integrated sterile fluid pathway connections to drug containers. Because the fluid path is disconnected until drug delivery is desired by the user, the sterility of the fluid pathway connection, the drug container, the drug fluid, and the device as a whole is maintained. Furthermore, the novel configurations of the fluid pathway connections and drug pumps of the present invention maintain the sterility of the fluid path through operation of the device. Because the path that the drug fluid travels within the device is entirely maintained in a sterile condition, only these components need be sterilized during the manufacturing process. Such components include the drug container of the drive mechanism, the fluid pathway connection, the sterile fluid conduit, and the insertion mechanism. In at least one embodiment of the present invention, the power and control system, the assembly platform, the control arm, the activation mechanism, the housing, and other components of the drug pump do not need to be sterilized. This greatly improves the manufacturability of the device and reduces associated assembly costs. Accordingly, the devices of the present invention do not require terminal sterilization upon completion of assembly. A further benefit of the present invention is that the components described herein are designed to be modular such that, for example, the fluid pathway connection and other components of the device may be integrated into a housing and readily interface to function as a drug pump.

In a further embodiment, the present invention provides a method of assembly of an integrated sterile fluid pathway connection and drug container. The sterile fluid pathway connection may first be assembled and then attached, mounted, connected, or otherwise integrated into drug container such that at least a portion of the sliding pierceable seal is contained within the drug container. The drug container may then be filled with a fluid for delivery to the user and plugged with a plunger seal at an end opposite the sliding pierceable seal. The barrel may be filled with a drug fluid through the open proximal end prior to insertion of the plunger seal from the proximal end of the barrel. A drive mechanism may then be attached to the proximal end of the drug container such that a component of the drive mechanism is capable of contacting the plunger seal. An insertion mechanism may be assembled and attached to the other end of the fluid conduit. This entire sub-assembly, including drive mechanism, drug container, fluid pathway connection, fluid conduit, and insertion mechanism may be sterilized, as described above, before assembly into a drug pump. Certain components of this sub-assembly may be mounted to an assembly platform within the housing or directly to the interior of the housing, while other components may be mounted to a guide, channel, or other component or aspect for activation by the user. A method of manufacturing a drug pump includes the step of attaching both the fluid pathway connection and drug container, either separately or as a combined component, to an assembly platform or housing of the drug pump. The method of manufacturing further includes attachment of the drive mechanism, drug container, and insertion mechanism to the assembly platform or housing. The additional components of the drug pump, as described herein, including the power and control system, the activation mechanism, and the control arm may be attached, preformed, or pre-assembled to the assembly platform or housing. An adhesive patch and patch liner may be attached to the housing surface of the drug pump that contacts the user during operation of the device.

A method of operating the drug pump includes one or more of the following steps: activating, by a user, the activation mechanism; displacing a control arm to actuate an insertion mechanism; activating a drive control mechanism to push the plunger seal, connect the sterile fluid pathway connection, and drive fluid drug flow through the drug pump, wherein translating the fluid pathway connection causes a piercing member to penetrate a sliding pierceable seal to thereby open a fluid path from the drug container to the fluid conduit. The drive control mechanism may be activated by actuating a power and control system. The method may further include the step of: engaging an optional on-body sensor prior to activating the activation mechanism. Furthermore, the method of operation may include translating a plunger seal within the drive control mechanism and drug container to force fluid drug flow through the drug container, the fluid pathway connection, the fluid conduit, and the insertion mechanism for delivery of the fluid drug to the body of a user.

The novel devices of the present invention provide container connections which maintain the sterility of the fluid pathway and which are integrated into the drug container, and drug delivery pumps which incorporate such integrated sterile fluid pathway connections to drug containers. Such devices are safe and easy to use, and are aesthetically and ergonomically appealing for self-administering patients. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein.

DETAILED DESCRIPTION

Figure 1A:
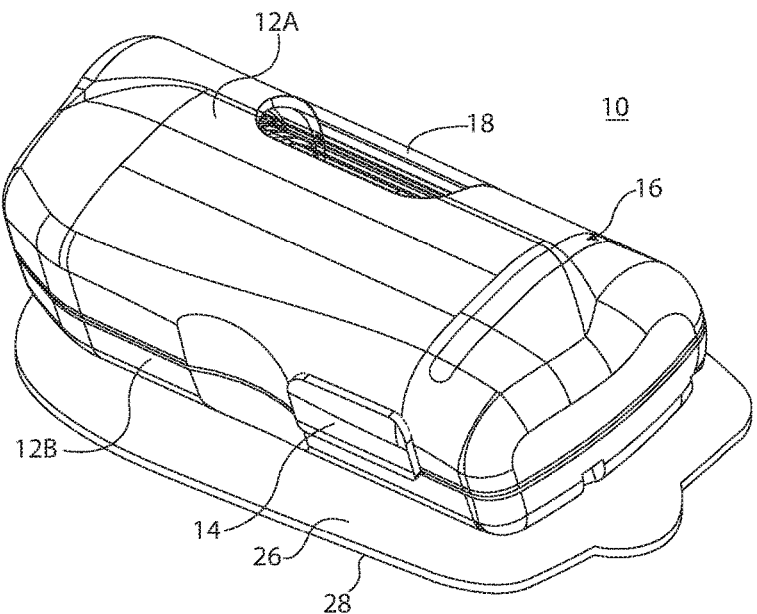
FIG. 1A shows an isometric view of a drug delivery pump having an integrated sterile fluid pathway connection and drug container, according to one embodiment of the present invention.

As used herein to describe the integrated sterile fluid pathway connection and drug containers, drug delivery pumps, or any of the relative positions of the components of the present invention, the terms "axial" or "axially" refer generally to a longitudinal axis "A" around which the drive mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of the pumps. According to various aspects and embodiments described herein, reference is made to a "biasing member", which may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring, preferably a compression spring.

The novel devices of the present invention provide container connections which maintain the sterility of the fluid pathway and which are integrated into the drug container, and drug delivery pumps which incorporate such integrated sterile fluid pathway connections to drug containers. Such devices are safe and easy to use, and are aesthetically and ergonomically appealing for self-administering patients. The devices described herein incorporate features which make activation, operation, and lock-out of the device simple for even untrained users. The novel devices of the present invention provide these desirable features without any of the problems associated with known prior art devices. Certain non-limiting embodiments of the novel drug delivery pumps, fluid pathway connections, and their respective components are described further herein with reference to the accompanying figures.

Figure 1B:
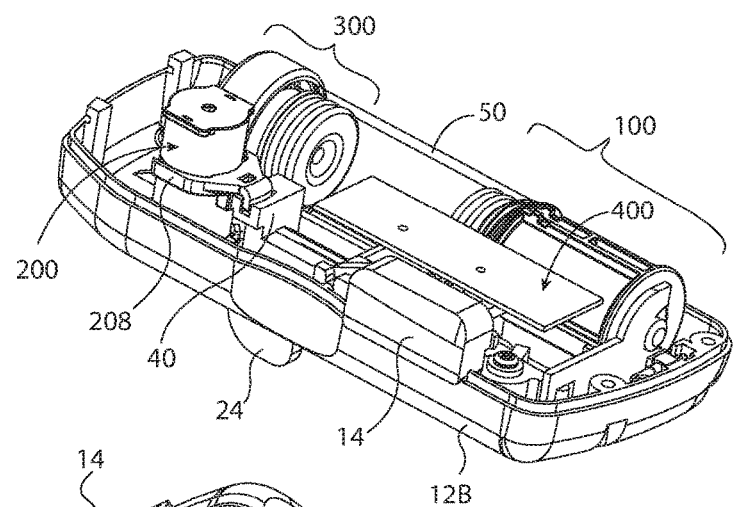
FIG. 1B shows an isometric view of the interior components of the drug delivery pump shown in FIG. 1A.
Figure 1C:
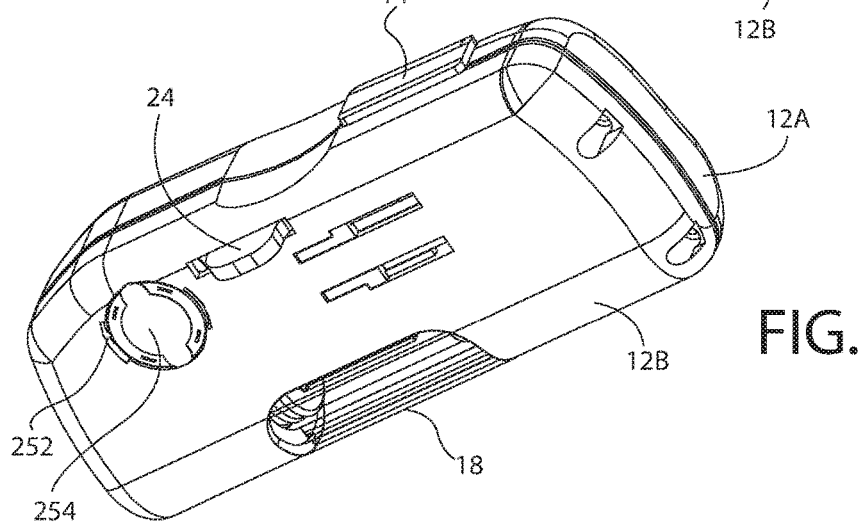
FIG. 1C shows an isometric view of the bottom of the drug delivery pump shown in FIG. 1A.

As used herein, the term "pump" is intended to include any number of drug delivery systems which are capable of dispensing a fluid to a user upon activation. Such drug delivery systems include, for example, injection systems, infusion pumps, bolus injectors, and the like. FIGS. 1A-1C show an exemplary drug delivery device according to at least one embodiment of the present invention. The drug delivery device may be utilized to administer delivery of a drug treatment into a body of a user. As shown in FIGS. 1A-1C, the drug pump 10 includes a pump housing 12. Pump housing 12 may include one or more housing sub-components which are fixedly engageable to facilitate easier manufacturing, assembly, and operation of the drug pump. For example, drug pump 10 includes a pump housing 12 which includes an upper housing 12A and a lower housing 12B. The drug pump may further include an activation mechanism 14, a status indicator 16, and a window 18. Window 18 may be any translucent or transmissive surface through which the operation of the drug pump may be viewed. As shown in FIG. 1B, drug pump further includes a sterile fluid conduit (not visible), a drive mechanism 100 having a drug container 50, an insertion mechanism 200, a sterile fluid pathway connection 300, and a power and control system 400. One or more of the components of such drug pumps may be modular in that they may be, for example, pre-assembled as separate components and configured into position within the housing of the drug pump 10 during manufacturing.

The pump housing 12A, 12B contains all of the device components and provides a means of removably attaching the device 10 to the skin of the user. The pump housing 12A, 12B also provides protection to the interior components of the device 10 against environmental influences. The pump housing 12A, 12B is ergonomically and aesthetically designed in size, shape, and related features to facilitate easy packaging, storage, handling, and use by users who may be untrained and/or physically impaired. Furthermore, the external surface of the pump housing 12A, 12B may be utilized to provide product labeling, safety instructions, and the like. Additionally, as described above, housing 12A, 12B may include certain components, such as status indicator 16 and window 18, which may provide operation feedback to the user.

In at least one embodiment, the drug pump 10 provides an activation mechanism 14 that is displaced by the user to trigger the start command to the power and control system 400. In a preferred embodiment, the activation mechanism is a start button 14 that is located through the pump housing 12A, 12B, such as through an aperture between upper housing 12A and lower housing 12B, and which contacts a control arm 40 of the power and control system 400. In at least one embodiment, the start button 14 may be a push button, and in other embodiments, may be an on/off switch, a toggle, or any similar activation feature known in the art. The pump housing 12A, 12B also provides a status indicator 16 and a window 18. In other embodiments, one or more of the activation mechanism 14, the status indicator 16, the window 18, and combinations thereof may be provided on the upper housing 12A or the lower housing 12B such as, for example, on a side visible to the user when the drug pump 10 is placed on the body of the user. Housing 12A, 12B is described in further detail hereinafter with reference to other components and embodiments of the present invention.

Drug pump is configured such that, upon activation by a user (such as by depression) of the activation mechanism, the drug pump is initiated to: insert a fluid pathway, such as a needle or cannula, into the user; enable, connect, or open necessary fluid pathway connections between a drug container, a fluid pathway, and a sterile fluid conduit; and force drug fluid stored in the drug container through the fluid pathway and fluid conduit for delivery into a user. One or more optional safety mechanisms may be utilized, for example, to prevent premature activation of the drug pump. For example, an optional on-body sensor 24 (shown in FIGS. 1B and 1C) may be provided in at least one embodiment as a safety feature to ensure that the power and control system 400, and/or the activation mechanism, cannot be engaged unless the drug pump 10 is in contact with the body of the user. In one such embodiment, the on-body sensor 24 is located on the bottom of lower housing 12B where it may come in contact with the user's body. Upon displacement of the on-body sensor 24, depression of the activation mechanism is permitted. Accordingly, in at least one embodiment the on-body sensor 24 is a mechanical safety mechanism, such as for example a mechanical lock out, that prevents triggering of the drug pump 10 by the activation mechanism 14. In another embodiment, the on-body sensor may be an electro-mechanical sensor such as a mechanical lock out that sends a signal to the power and control system 400 to permit activation. In still other embodiments, the on-body sensor can be electrically based such as, for example, a capacitive- or impedance-based sensor which must detect tissue before permitting activation of the power and control system 400. These concepts are not mutually exclusive and one or more combinations may be utilized within the breadth of the present invention to prevent, for example, premature activation of the drug pump 10. In a preferred embodiment, the drug pump 10 utilizes one or more mechanical on-body sensors. Additional integrated safety mechanisms are described herein with reference to other components of the novel drug pumps.

Power and Control System:

The power and control system 400 may include a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the user and may interface with one or more other components of the drug pump 10, such as the drive mechanism 100. In one embodiment, the power and control system 400 interfaces with the control arm 40 to identify when the on-body sensor 24 and/or the activation mechanism 14 have been activated. The power and control system 400 may also interface with the status indicator 16 of the pump housing 12A, 12B, which may be a transmissive or translucent material which permits light transfer, to provide visual feedback to the user. The power and control system 400 may interface with the drive mechanism 100 and/or the integrated sterile fluid pathway connection 300 and drug container 50 through one or more interconnects to relay status indication, such as activation, drug delivery, and/or end-of-dose, to the user. Such status indication may be presented to the user via tactile feedback, such as vibration; auditory tones, such as through the audible alarms; and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may also maintain the energy stored in the power source during storage, transport, and the like.

The power and control system 400 may be configured to provide a number of different status indicators to the user. For example, the power and control system 400 may be configured such that after the on-body sensor and/or trigger mechanism have been pressed, the power and control system 400 provides a ready-to-start status signal via the status indicator 16 if device start-up checks provide no errors. After providing the ready-to-start status signal and, in an embodiment with the optional on-body sensor, if the on-body sensor remains in contact with the body of the user, the power and control system 400 will power the drive mechanism 100 to begin delivery of the drug treatment through the integrated sterile fluid pathway connection 300 and sterile fluid conduit 30. In a preferred embodiment of the present invention, the insertion mechanism 200 and the drive mechanism 100 may be caused to activate directly by user operation of the activation mechanism 14. The integrated sterile fluid pathway connection is connected (i.e., the fluid pathway is opened) by the pneumatic force of the drug fluid within the drug container 50 created by activation of the drive mechanism 100, as is detailed further herein. During the drug delivery process, the power and control system 400 is configured to provide a dispensing status signal via the status indicator 16. After the drug has been administered into the body of the user and after the end of any additional dwell time, to ensure that substantially the entire dose has been delivered to the user, the power and control system 400 may provide an okay-to-remove status signal via the status indicator 16. This may be independently verified by the user by viewing the drive mechanism and delivery of the drug dose within the drug container through the window 18 of the pump housing 12A, 12B. Additionally, the power and control system 400 may be configured to provide one or more alert signals via the status indicator 16, such as for example alerts indicative of fault or operation failure situations.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 14 of the drug pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Insertion Mechanism:

A number of insertion mechanisms may be utilized within the drug pumps of the present invention. In at least one embodiment, the insertion mechanism 200 includes an insertion mechanism housing having one or more lockout windows, and a base for connection to the assembly platform and/or pump housing (as shown in FIG. 1B and FIG. 1C). The connection of the base to the interior of the pump housing 12A, 12B may be, for example, such that the bottom of the base is permitted to pass-through a hole in the bottom housing 12B to permit direct contact of the base to the body of the user. In such configurations, the bottom of the base 252 may include a sealing membrane 254 that is removable prior to use of the drug pump 10. The insertion mechanism may further include one or more insertion biasing members, a needle, a retraction biasing member, a cannula, and a manifold. The manifold may connect to sterile fluid conduit 30 to permit fluid flow through the manifold, the needle and/or cannula, and into the body of the user during drug delivery.

As used herein, "needle" is intended to refer to a variety of needles including but not limited to conventional hollow needles, such as a rigid hollow steel needles, and solid core needles commonly referred to as a "trocars." In a preferred embodiment, the needle is a 27 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base 252 may be closed from non-sterile environments as well, such as by for example a sealing membrane 254 (shown in FIG. 1C).

According to at least one embodiment of the present invention, the insertion mechanism is substantially similar to that described in International Patent Application No. PCT/US2012/053174, which is included by reference herein in its entirety for all purposes. The insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. As shown in FIG. 1B, the lockout pin(s) 208 may be directly displaced by user depression of the activation mechanism 14. As the user disengages any safety mechanisms, such as an optional on-body sensor 24, the activation mechanism 14 may be depressed to initiate the drug pump. Depression of the activation mechanism 14 may directly cause translation or displacement of control arm 40 and directly or indirectly cause displacement of lockout pin(s) 208 from their initial position within corresponding locking windows of insertion mechanism 200. Displacement of the lockout pin(s) 208 permits insertion biasing member to decompress from its initial compressed, energized state. This decompression of the insertion biasing member drives the needle and the cannula into the body of the user. At the end of the insertion stage, the retraction biasing member is permitted to expand in the proximal direction from its initial energized state. This axial expansion in the proximal direction of the retraction biasing member retracts the needle while maintaining the cannula in fluid communication with the body of the user. Accordingly, the insertion mechanism may be used to insert a needle and cannula into the user and, subsequently, retract the needle while retaining the cannula in position for drug delivery to the body of the user. In an alternative embodiment, the needle may be retained in fluid communication within the body with or without the presence of a flexible cannula. A number of insertion mechanisms may be utilized, as would readily be appreciated by an ordinarily skilled artisan.

Figure 2A:
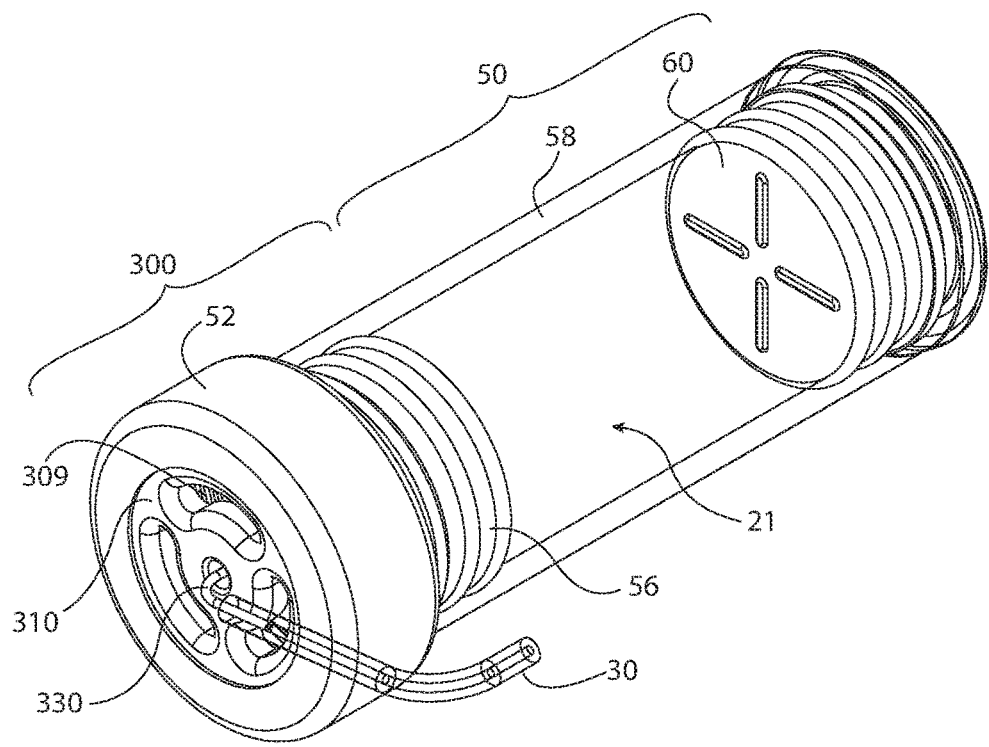
FIG. 2A shows an isometric view of an integrated sterile fluid pathway connection and drug container, according to one embodiment of the present invention.

Drive Mechanism:

A number of drive mechanisms may be utilized to force fluid from a drug container for delivery into the body of a user. In one such embodiment, the drive mechanism 100 may be substantially similar to that described in International Patent Application No. PCT/US2012/053241, which is included by reference herein in its entirety for all purposes. As shown in FIG. 2A, a drug container may have a drug chamber 21 within the barrel 58 between a sliding pierceable seal 56 and a plunger seal 60. The drug chamber 21 may contain a drug fluid for delivery through integrated sterile fluid pathway connection, the insertion mechanism, and drug pump into the body of the user. The seals described herein may be comprised of a number of materials but are, in a preferred embodiment, comprised of one or more elastomers or rubbers. The drive mechanism 100 may contain one or more drive biasing members to drive the plunger seal 60. The components of the drive mechanism function to force a fluid from the drug chamber 21 out through the sliding pierceable seal, or preferably through the piercing member 330 of the fluid pathway connection 300, for delivery through the fluid pathway connection 300, sterile fluid conduit 30, and insertion mechanism 200 into the body of the user. For clarity, the piercing member 330 may be an aspect of fluid conduit 30 or may be a separate component from fluid conduit 30, as would readily be appreciated by one having ordinary skill in the art.

In one particular embodiment, the drive mechanism 100 employs one or more compression springs as the biasing member(s). Upon activation of the drug pump by the user, the power and control system 400 may be actuated to directly or indirectly release the compression spring(s) from an energized state. Upon release, the compression spring(s) may bear against and act upon the plunger seal 60 to force the fluid drug out of the drug chamber 21 of the drug container. As the plunger seal 60 asserts a force on the drug fluid, pneumatic pressure builds by compression of the drug fluid and the force is relayed to the sliding pierceable seal 56. The sliding pierceable seal 56 is caused to slide towards the cap 52, causing it to be pierced by the piercing member retained within the integrated sterile fluid pathway connection 300. Accordingly, the integrated sterile fluid pathway connection 300 is connected (i.e., the fluid pathway is opened) by the pneumatic force of the drug fluid within the drug chamber 21 created by activation of the drive mechanism 100, as is detailed further herein. Once the integrated sterile fluid pathway connection 300 is connected or opened, drug fluid is permitted to flow from the drug container, through the integrated sterile fluid pathway connection, sterile fluid conduit 30, and insertion mechanism, and into the body of the user for drug delivery. In at least one embodiment, the fluid flows through only a manifold and a cannula and/or needle of the insertion mechanism, thereby maintaining the sterility of the fluid pathway before and during drug delivery. Such components and their functions are described in further detail hereinafter.

The components of the drive mechanism 100, upon activation, may be used to drive axial translation in the distal direction of the plunger seal of the drug container. Optionally, the drive mechanism 100 may include one or more compliance features which enable additional axial translation of the plunger seal to, for example, ensure that substantially the entire drug dose has been delivered to the user and make sure that the feedback contact mechanisms have connected. Additionally or alternatively, the plunger seal and/or the sliding pierceable seal may have some compressibility permitting a compliance push of drug fluid from the drug container. The drive mechanism 100 may similarly include one or more status indication mechanisms, such as interconnects and contacts, to measure and communicate the status of the drive mechanism before, during, and after operation of the drive mechanism and the device to the user. Such components and functionality are described in further detail herein. Furthermore, the drive mechanism 100 may include one or more safety mechanisms, such as premature activation prevention mechanisms, to enhance the safety and usability of the mechanism and the device.

Integrated Sterile Fluid Pathway Connection:

The novel embodiments of the present invention provide integrated sterile fluid pathway connections and drug containers, and drug pumps which utilize such connections which are capable of maintaining the sterility of the fluid pathway before, during, and after operation of the device, and which enable active safety controls for the device. Integration of the fluid pathway connection into a portion of the drug container helps ensure container integrity and sterility of the fluid pathway. Additionally, by integrating the sterile fluid pathway connection into a portion of the drug container, the connection for fluid transfer can be controlled by the user (i.e., user-activated) and enabled by the function of the drive mechanism. Accordingly, user-activation steps and the internal operation of the drug pump can be greatly simplified by the novel integrated sterile fluid pathway connections of the present invention.

Figure 2B:
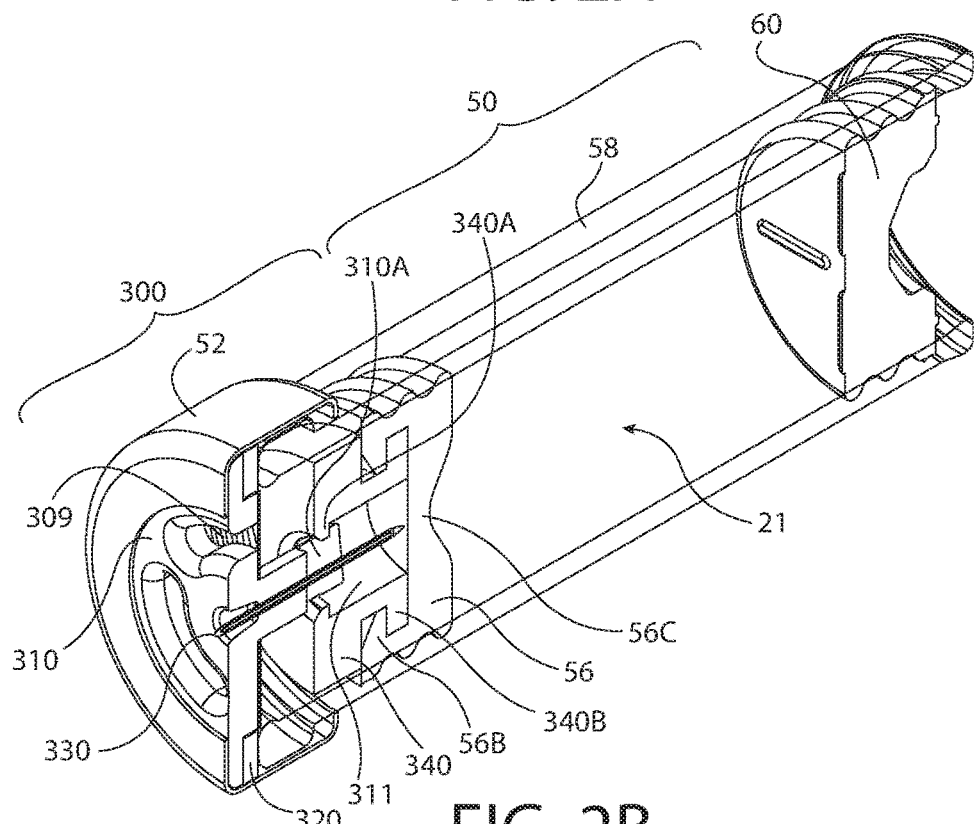
FIG. 2B shows a cross-sectional view of the integrated sterile fluid pathway connection and drug container shown in FIG. 2A.

In one embodiment, the fluid pathway connection 300 includes a sterile fluid conduit 30, a piercing member 330, a connection hub 310, and a sliding pierceable seal 56. As shown in FIGS. 2A and 2B, the fluid pathway connection 300 may optionally include a seal mount 340 upon which the sliding pierceable seal 56 may be mounted to interface with connection hub 310. A permeable, semi-permeable, or porous membrane, such as a filter 309, may be utilized to allow venting of air from within the fluid pathway connection 300 during operation of the device. The filter 309 may be attached, mounted, bonded, over-molded, co-molded, pre-formed, or otherwise connected to enclose the sterile cavity 311 within the connection hub 310. The term "enclose" or "enclosure" is used herein to define at least a semi-permeable or porous confined area that is capable of being sterilized, evacuated by vacuum, and vented, but not penetrable by microorganisms, contaminants, or other undesirable environmental factors. For example, the filter 309 may be over-molded at least partially within the connection hub 310 to separate the sterile cavity 311 from the outside environment. The filter is a membrane, preferably a semi-permeable membrane, which allows the venting of air during the actuation of the sliding pierceable seal 56, the fluid pathway connection 300, and device 10. While the filter may be permeable to sterilization methods, which would readily be appreciated by one having ordinary skill in the art, the filter may be utilized to maintain a sterile barrier to prevent exposure of the piercing member 330 to microorganisms, contaminants, or other undesirable environmental factors.

Additionally, the fluid pathway connection 300 may optionally include one or more gaskets, O-rings, or other sealing members, such as gasket 320 compressed to seal between barrel 58, connection hub 310, and cap 52. The cap 52 may be a separate component or may be an aspect of connection hub 310 capable of mounting to the barrel 58. As shown in FIG. 1C, the fluid pathway connection 300 may be attached to (i.e., integrated with) a drug container 50 and mounted, by a number of known methods, either fixedly or removably to an assembly platform or housing of the drug pump. The assembly platform may be a separate component from the housing, or may be a unified component of the housing such as a pre-formed mounting aspect on the interior surfaces of the housing. In either configuration, the sterility of the fluid pathway is maintained, the pathway for fluid flow is not connected until desired by the user, and user-initiated activation causes the connection of the drug chamber and the fluid pathway connection. The fluid pathway connection may, optionally, further include one or more separate flow restrictors and/or one or more of piercing member 330 and fluid conduit 30 may additionally function as flow restrictors.

Upon proper activation of the device 10 by the user, the fluid pathway connection 300 is connected to the drug container 50, thereby enabling fluid flow from the drug chamber 21 (as may be forced by the drive mechanism 100), through the fluid pathway connection 300, the fluid conduit 30, the insertion mechanism 200 and into the body of the user. Such connection between the fluid pathway connection 300 and the drug chamber 21 may be facilitated by a piercing member 330, such as a needle, penetrating a sliding pierceable seal 56 (shown in the transition between FIGS. 4A and 4B). As the plunger seal 60 asserts a force on the drug fluid, pneumatic pressure builds by compression of the drug fluid and the force is relayed to the sliding pierceable seal 56. The sliding pierceable seal 56 is caused to slide towards the cap 52, causing it to be pierced by the piercing member retained within the integrated sterile fluid pathway connection 300. Accordingly, the integrated sterile fluid pathway connection 300 is connected (i.e., the fluid pathway is opened) by the pneumatic force of the drug fluid within the drug chamber 21 created by activation of the drive mechanism 100, as is detailed further herein.

The sterility of the fluid pathway connection is initially maintained by performing the connection within a sterile cavity 311 between connection hub 310, sliding pierceable seal 56, and optionally seal mount 340. In at least one embodiment, the sterility of cavity 311 is maintained by a filter 309 connected to, or part of, the connection hub 310. The filter 309 may be, for example, a semi-permeable membrane that allows the venting of air during the actuation and translation of the sliding pierceable seal 56. While the filter may be permeable to sterilization methods, which would readily be appreciated by one having ordinary skill in the art, the filter may be utilized to maintain a sterile barrier to prevent expose of the piercing member 330 to microorganisms, contaminants, or other undesirable environmental factors. Upon substantially simultaneous activation of the insertion mechanism 200, the fluid pathway between drug chamber 21 and insertion mechanism 200 is complete to permit drug delivery into the body of the user. Because the fluid pathway connection is not in fluid connection or communication with the drug chamber until activation of the drug pump and drive mechanism, fluid flow from the drug container is prevented until desired by the user. This provides an important safety feature to the user while also maintaining the container integrity of the drug container and sterility of the fluid pathway.

FIGS. 2A and 2B show an initial configuration of the sterile fluid pathway connection 300 integrated with a drug container 50 having a drug chamber 21 and a plunger seal 60. The fluid pathway connection 300 may be mounted, connected, or otherwise attached to the drug container 50 at an end opposite the plunger seal 60. At least in an initial configuration, a piercing member 330 is maintained within a sterile cavity 311 with a proximal end adjacent to, or contacting, a sliding pierceable seal 56 of the fluid pathway connection 300. Preferably, the sterility of cavity 311 and piercing member 330 is maintained by a filter 309 which may be between the sterile cavity 311 and the outside environment. In at least one embodiment, the filter 309 is connected to, or part of, the connection hub 310 to enclose the sterile cavity 311 from the outside environment. Accordingly, the fluid pathway connection 300 of the present invention, in at least one embodiment, is mounted to and integrated with a drug container 50. The piercing member 330 may be a number of cannulas or conduits, such as rigid needles, and may be comprised of a number of materials, such as steel. In at least one embodiment, the piercing member 330 is a rigid steel needle. The sliding pierceable seal 56 may be mounted directly to, and translatable upon, a connection post 310A of the connection hub 310. Such an arrangement permits the sliding pierceable seal 56 to translate towards the cap 52 but not towards the plunger seal 60. This is a desirable feature which permits the drug chamber 21 of the drug container 50 to be evacuated, such as by vacuum, prior to filling with a drug fluid without compromising the function of the sterile fluid pathway connection 300.

As the device is activated and the drive mechanism pushes the plunger seal 60 to begin drug delivery, pneumatic pressure builds up in the drug fluid within the drug chamber 21. The pneumatic pressure applies a force to the sliding pierceable seal 56 causing it to translate upon connection post 310A towards cap 52. This translation of the sliding pierceable seal 56 and the substantially fixed position of the piercing member 330 causes piercing member 330 to pierce the sliding pierceable seal 56 at seal barrier 56C, thereby opening or otherwise connecting the fluid pathway between the drug chamber 21, the piercing member 330, and the fluid conduit 30. In an initial position, the distal end of the piercing member 330 may reside adjacent to, or in contact with, the seal barrier 56C of the sliding pierceable seal 56 to, for example, minimize the distance of translation of the sliding pierceable seal 56 to become pierced and open the drug container to the fluid pathway. In one particular embodiment, the distal end of the piercing member 330 may reside at least partially within the seal barrier 56C of the sliding pierceable seal 56, yet not fully passing therethrough until activation of the device by the user.

In at least one embodiment of the present invention, as shown in FIGS. 2A, 2B, 5A, and 5B, among others, a seal mount 340 may be utilized to mount the sliding pierceable seal 56 upon and to slidably engage the connection post 310A of the connection hub 310. The sliding pierceable seal 56 may be removably attached to the seal mount 340 by a number of means known in the art such as, for example, removable snap-fit engagement between seal ledge 56B and corresponding seal mount rim 340B. Similarly, the seal mount 340 may be slidably attached to connection hub 310 at connection post 310A. A number of means known in the art may be utilized to facilitate this slidable attachment such as, for example, engagement between connection prongs 310B of the connection hub 310 and corresponding connection rim 340A of the seal mount 340. These components are more clearly visible in FIGS. 3A, 3B, and 5B. Such an arrangement permits the sliding pierceable seal 56 and the seal mount 340 to translate towards the cap 52 but not towards the plunger seal 60. This is a desirable feature which permits the drug chamber 21 of the drug container 50 to be evacuated, such as by vacuum, prior to filling with a drug fluid without compromising the function of the sterile fluid pathway connection 300.

Figure 5A:
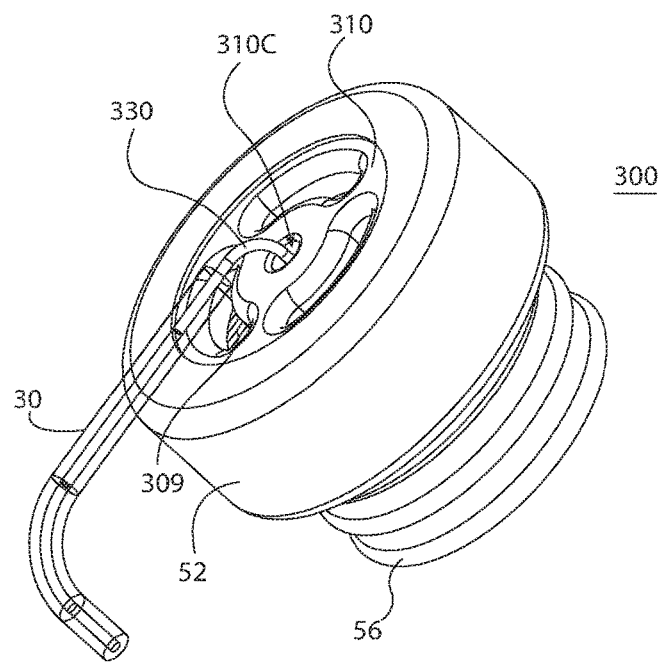
FIG. 5A shows an isometric view, from the proximal perspective, of the integrated sterile fluid pathway connection according to one embodiment of the present invention.
Figure 5B:
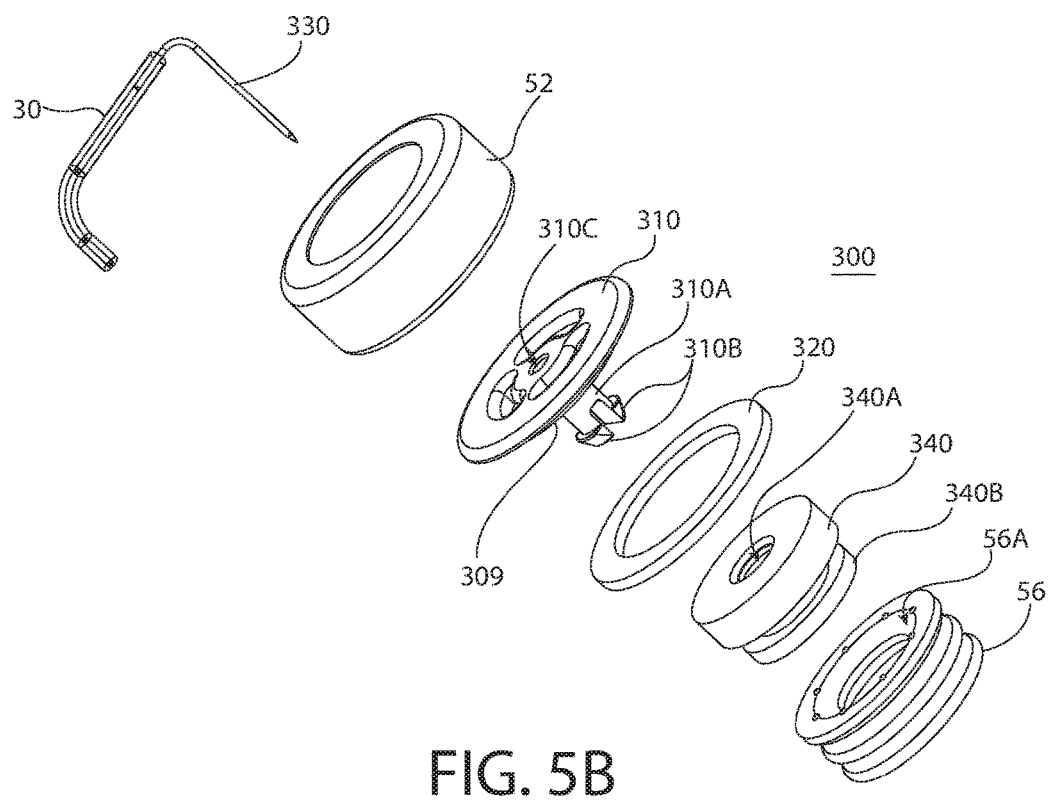
FIG. 5B shows an exploded view, from the proximal perspective, of the integrated sterile fluid pathway connection shown in FIG. 5A.
Figure 5C:
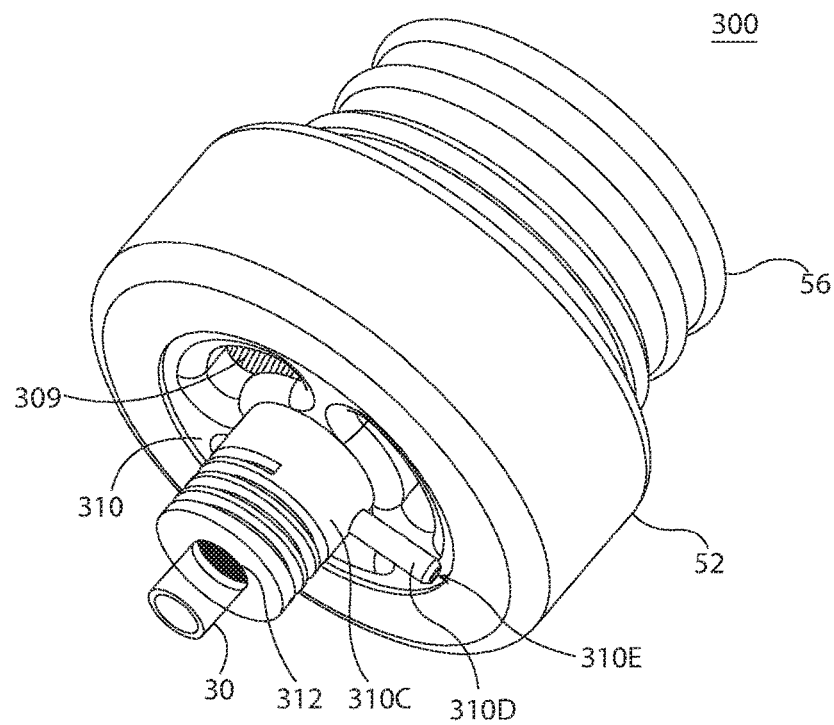
FIG. 5C shows an isometric view, from the proximal perspective, of the integrated sterile fluid pathway connection, according to another embodiment of the present invention.
Figure 5D:
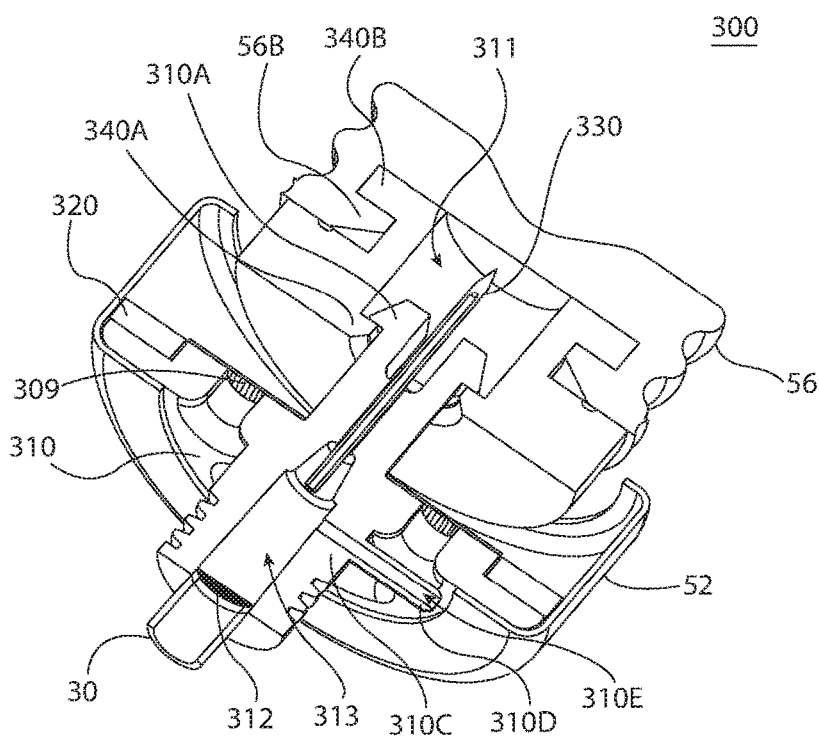
FIG. 5D shows a cross-sectional view of the integrated sterile fluid pathway connection shown in FIG. 5C.

As is visible in the embodiment shown in FIGS. 2A, 2B, 5A, and 5B, among others, the fluid conduit 30 may be connected directly to piercing member 330. Alternatively, as shown in FIGS. 5C and 5D, the fluid conduit 30 may be connected to a header 310C of the connection hub 310 at conduit port 312. The piercing member 330 may reside within header 310C, such as within a chamber 313. Header 310C may also have a vacuum port 310D with a channel 310E that leads into chamber 313. Conduit port 312 and vacuum port 310D may contain membranes or seals, such as one-way seals, which permit fluid flow out of chamber 313 through the respective ports but not permit fluid flow into the chamber 313 through said ports. Additionally, or alternatively, conduit port 312 and vacuum port 310D may be plugged at certain points of assembly or operation. For example, vacuum port 310D may be utilized to evacuate the chamber 313, the piercing member 330, and the sterile cavity 311 during manufacturing, assembly, or at any point prior to operation of the device; and then vacuum port 310D may be plugged after the evacuation has been completed.

Figures 3A, 3B:
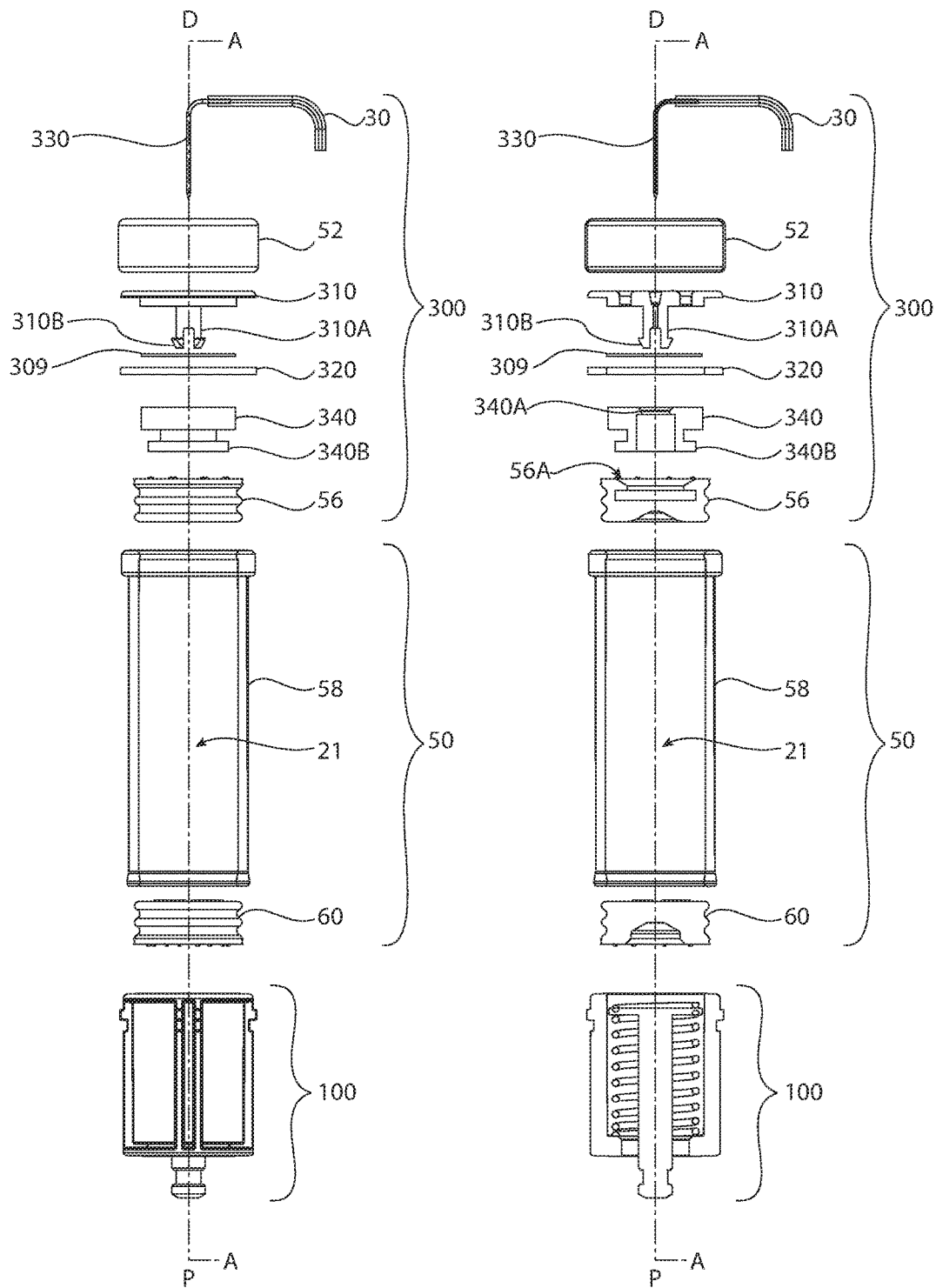
FIG. 3A shows an exploded view of an integrated sterile fluid pathway connection and drug container, exploded along a longitudinal axis "A," according to at least one embodiment of the present invention.
FIG. 3B shows a cross-sectional exploded view of the integrated sterile fluid pathway connection and drug container shown in FIG. 3A.

FIG. 3A shows an exploded view of an integrated sterile fluid pathway connection and drug container, exploded along a longitudinal axis "A," according to at least one embodiment of the present invention. FIG. 3B shows a cross-sectional exploded view of the same embodiment. As detailed herein, the sterile fluid pathway connection 300 may be integrated into the drug container 50 at an end opposite the plunger seal 60. An exemplary drive mechanism 100, as detailed above, is shown in these figures to clarify the orientation of these components in at least one embodiment of the present invention. The components of the novel sterile fluid pathway connection 300 may be pre-assembled, to appear as shown in FIG. 5A, and attached, mounted, connected, or otherwise mated with the drug container 50. Alternatively, the components of the sterile fluid pathway connection 300 may be assembled directly into the drug container 50. As would be readily appreciated by an ordinary skilled artisan, a number of glues or adhesives, or other connection methods such as snap-fit, interference fit, screw fit, fusion joining, welding, ultrasonic welding, laser welding, and mechanical fastening, and the like may optionally be utilized to engage one or more of the components described herein. For example, a glue may be utilized between the distal end of the barrel 58 and the connection hub 310 and/or the optional gasket 320. Additionally or alternatively, the components of the sterile fluid pathway connection 300 may be mounted to barrel 58 and held in place by crimping cap 52 to a distal aspect of barrel 58, such as to a flanged aspect of barrel 58.

Figure 4A:
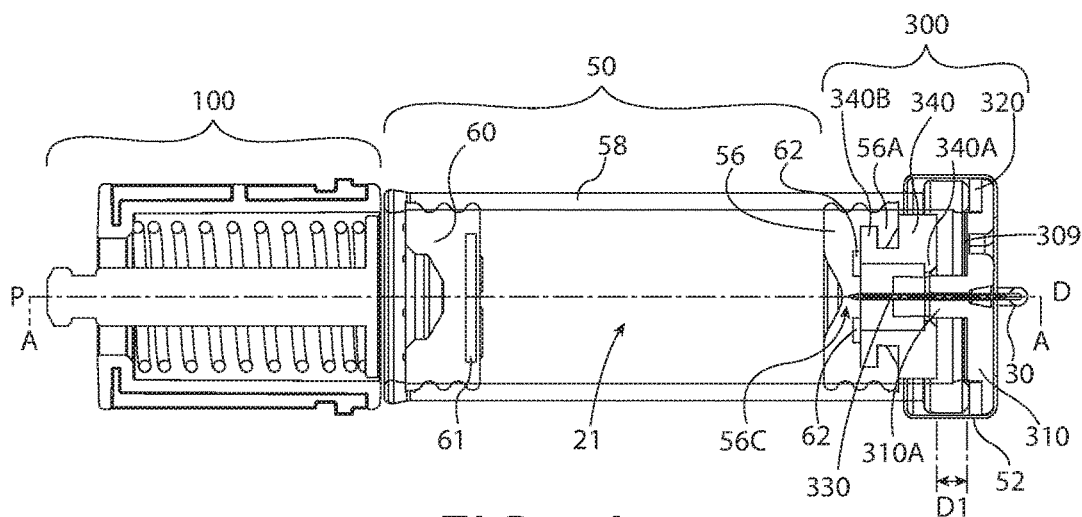
FIG. 4A shows a cross-sectional view of an integrated sterile fluid pathway connection and drug container, as shown in FIG. 2A, prior to user activation.
Figure 4B:
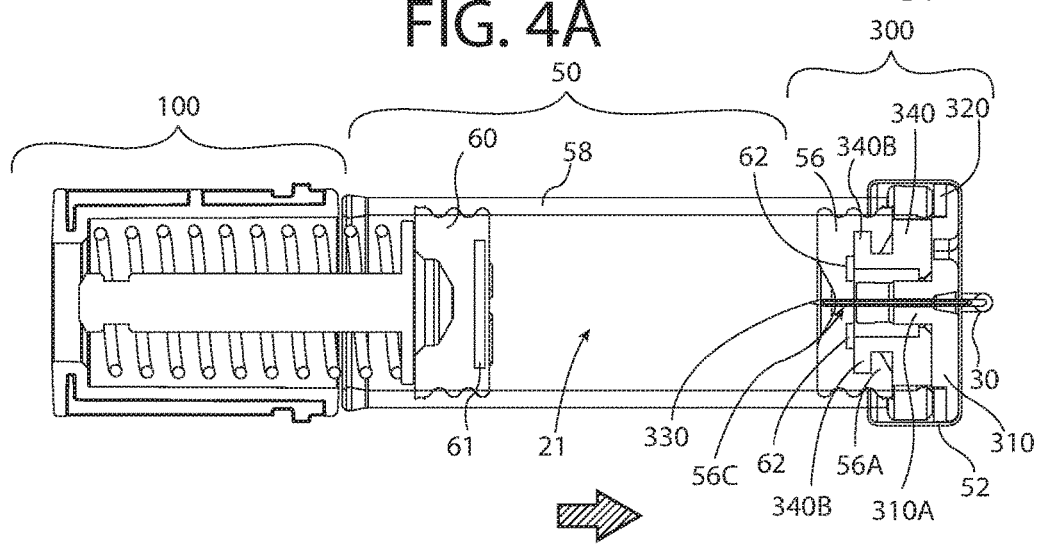
FIG. 4B shows a cross-sectional view of an integrated sterile fluid pathway connection and drug container, as shown in FIG. 2A, with the fluid pathway connected.
Figure 4C:
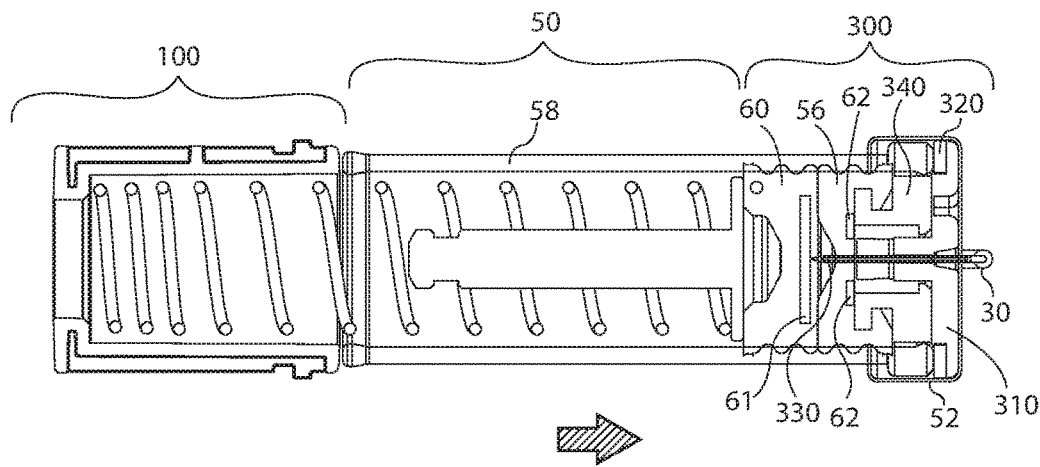
FIG. 4C shows a cross-sectional view of an integrated sterile fluid pathway connection and drug container, as shown in FIG. 2A, at the end of drug delivery.

FIGS. 4A-4C show a cross-sectional view of an integrated sterile fluid pathway connection and drug container as it progresses through the stages of use. FIG. 4A shows the sterile fluid pathway connection 300 prior to user activation of the device by the user. The piercing member 330 is initially maintained within a sterile cavity 311 with a proximal end adjacent to, or contacting, a sliding pierceable seal 56 of the fluid pathway connection 300. The sliding pierceable seal 56 may be removably attached to the seal mount 340 by a number of means known in the art such as, for example, removable snap-fit engagement between seal ledge 56B and corresponding seal mount rim 340B. Similarly, the seal mount 340 may be slidably attached to connection hub 310 at connection post 310A. In at least one embodiment, the sterility of cavity 311 is maintained by a filter 309. The filter 309 may be a permeable, semi-permeable, or porous membrane to allow venting of air from within the fluid pathway connection 300 during operation of the device and actuation and translation of the sliding pierceable seal 56. The filter 309 may be attached, mounted, bonded, over-molded, co-molded, pre-formed, or otherwise connected to enclose the sterile cavity 311 within the connection hub 310. For example, the filter 309 may be over-molded at least partially within the connection hub 310 to separate the sterile cavity 311 from the outside environment. While the filter may be permeable to sterilization methods, which would readily be appreciated by one having ordinary skill in the art, the filter may be utilized to maintain a sterile barrier to prevent exposure of the piercing member 330 to microorganisms, contaminants, or other undesirable environmental factors.

Whether or not the optional seal mount 340 is utilized in the sterile fluid connection 300, a distance D1 initially exists between the connection hub 310 and the sliding pierceable seal 56 and/or seal mount 340, as shown in FIG. 4A. A number of means known in the art may be utilized to facilitate this slidable attachment such as, for example, engagement between connection prongs 310B of the connection hub 310 and corresponding connection rim 340A of the seal mount 340. Such an arrangement permits the sliding pierceable seal 56 and the seal mount 340 to translate towards the cap 52 but not towards the plunger seal 60. This is a desirable feature which permits the drug chamber 21 of the drug container 50 to be evacuated at the proximal end, such as by vacuum, prior to filling with a drug fluid without compromising the function of the sterile fluid pathway connection 300. After filling the drug chamber with a drug fluid, a plunger seal 60 may be inserted into the drug container 50 to seal the proximal end. A drive mechanism 100 may then be attached to the proximal end of the drug container 50 or, alternatively, these components may be caused to come into contact upon assembly into the drug pump. As the device is activated and the drive mechanism 100 pushes the plunger seal 60 to begin drug delivery, pneumatic pressure builds up in the drug fluid within the drug chamber 21. The pneumatic pressure applies a force to the sliding pierceable seal 56 causing it to translate, with seal mount 340 when one is utilized, upon connection post 310A towards cap 52 (i.e., the distal end). As shown in FIG. 4B, this translation of the sliding pierceable seal 56 (in the direction of the hatched arrow) and the substantially fixed position of the piercing member 330 closes the distance D1 and causes piercing member 330 to pierce the sliding pierceable seal 56 at membrane 56A, thereby opening or otherwise connecting the fluid pathway between the drug chamber 21, the piercing member 330, and the fluid conduit 30. Once the fluid pathway is opened or connected, translation of the plunger seal 60 in the distal direction by the drive mechanism 100 causes drug fluid within drug chamber 21 to be forced through piercing member 330 and fluid conduit 30 for drug delivery to the user. A needle insertion mechanism, as described herein, may be connected at the other end of the fluid conduit 30 to insert a needle into the body of the user to facilitate fluid transfer to the user. FIG. 4C shows the components of the drive mechanism 100, drug container 50, and sterile fluid pathway connection 300 after substantially all of the drug fluid has been pushed out of the drug container 50. Because of the novel design of the fluid pathway connections 300 of the present invention and their integration within drug containers 50, sterility of the fluid pathway is maintained throughout transport, storage, and operation of the device; user-activation of the device is simplified; and the fluid pathway is only connected when desired by the user.

The novel integrated sterile fluid pathway connections of the present invention may additionally incorporate status indication into the drug dose delivery. Such status indication features may be incorporated into the drive mechanism 100, as described in International Patent Application No. PCT/US2012/053241 and incorporate herein by reference. Additionally or alternatively, such status indication features may be incorporated into the components of the sterile fluid pathway connection themselves. In one embodiment, one or more interconnects 61 are contained within, or proximal of, plunger seal 60. At the end of drug delivery, shown in FIG. 4C, the piercing member 330, itself, may be utilized to contact the, and/or as a contact for, interconnect 61 to open, close, or otherwise create a signal to the power and control system to provide feedback to the user. In another embodiment, one of either the interconnects 61 or the contacts 62 are contained within, or proximal of, plunger seal 60, while the other is contained within or distal of sliding pierceable seal 56. At the end of drug delivery, the interconnects and corresponding contacts are close enough to permit a signal to be sent to the power and control system to provide feedback to the user. A number of known interconnects and contacts, or similar components, are known in the art and may be utilized within the novel embodiments disclosed herein. As would readily be appreciated by one having ordinary skill in the art, a vast range of magnets, sensors, coils, and the like may be utilized to connect, transmit, or relay a signal for user feedback. Generally, any RLC circuit systems having a resistor, an inductor, and a capacitor, connected in series or in parallel, may be utilized for this purpose. For example, Hall effect sensors; giant magneto resistance (GMR) or magnetic field sensors; optical sensors; capacitive or capacitance change sensors; ultrasonic sensors; and/or linear travel, LVDT, linear resistive, or radiometric linear resistive sensors may be utilized as interconnects and corresponding contacts used to permit a signal to be sent to the power and control system to provide feedback to the user. The location of the contacts and interconnects may be interchanged or in a number of other configurations which permit completion of an electrical circuit or otherwise permit a transmission between the components.

By use of one or more status switch interconnects and one or more corresponding electrical contacts, the status of the drive mechanism before, during, and after operation can be relayed to the power and control system to provide feedback to the user. Such feedback may be tactile, visual, and/or auditory, as described above, and may be redundant such that more than one signals or types of feedback are provided to the user during use of the device. As described above, in at least one embodiment an end-of-dose status indication may be provided to the user once the status switch interconnect 132 is caused to contact electrical contact 134 at the end of axial travel of the plunger seal 60 within the barrel 58 of the drug container 50.

Additionally, the embodiments of the present invention provide end-of-dose compliance to ensure that substantially the entire drug dose has been delivered to the user and that the status indication features have been properly contacted to provide accurate feedback to the user. Through these mechanisms, confirmation of drug dose delivery can accurately be provided to the user or administrator. Accordingly, the novel devices of the present invention alleviate one or more of the problems associated with prior art devices, such as those referred to above. Optionally, the drive mechanism 100 may include one or more compliance features which enable additional axial translation of the plunger seal 60 to, for example, ensure that substantially the entire drug dose has been delivered to the user and make sure that the feedback contact mechanisms have connected. For example, in one embodiment of the present invention, as will be described further below, the drive mechanism 100 may be configured to drive further axial translation of at least a portion of the plunger seal 60 for a compliance push of the plunger seal, and/or of drug fluid, from the drug container. Additionally or alternatively, the plunger seal 60, itself, may have some compressibility permitting a compliance push. For example, when a pop-out plunger seal is employed, i.e., a plunger seal that is deformable from an initial state, the plunger seal may be caused to deform or "pop-out" to provide a compliance push. Similarly, the plunger seal may be porous, compressible, deformable, or the like to itself be capable of providing a compliance push.

Figure 6A:
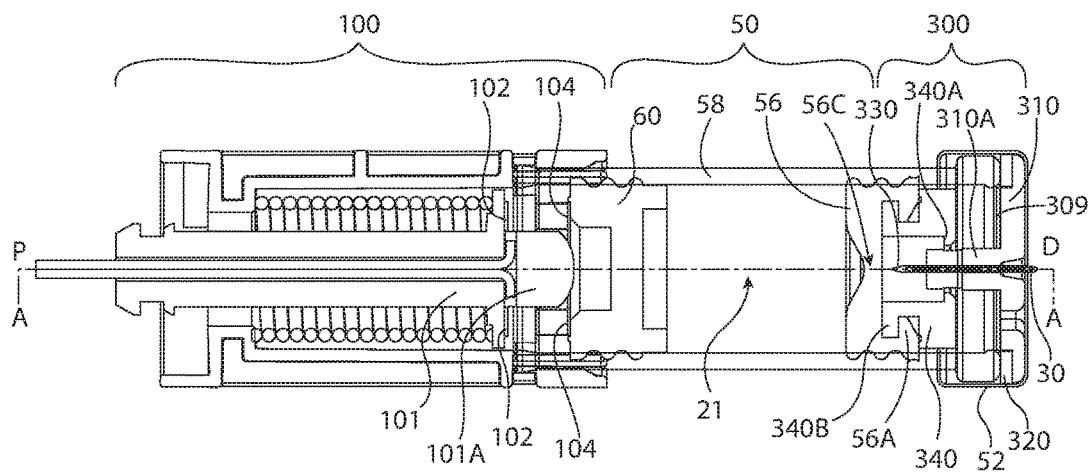
FIG. 6A shows a cross-sectional view of an integrated sterile fluid pathway connection and drug container, according to another embodiment of the present invention, prior to user activation.
Figure 6B:
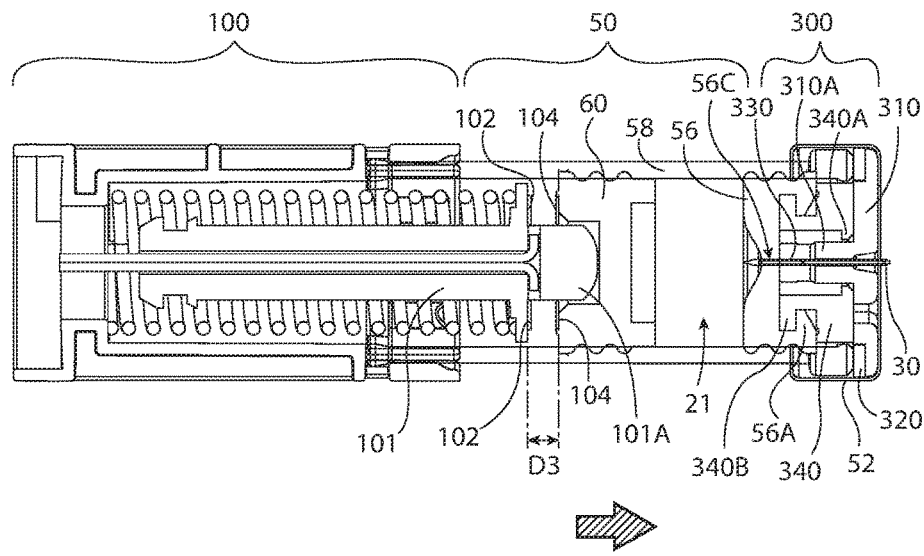
FIG. 6B shows a cross-sectional view of the integrated sterile fluid pathway connection and drug container shown in FIG. 6A, with the fluid pathway connected.
Figure 6C:
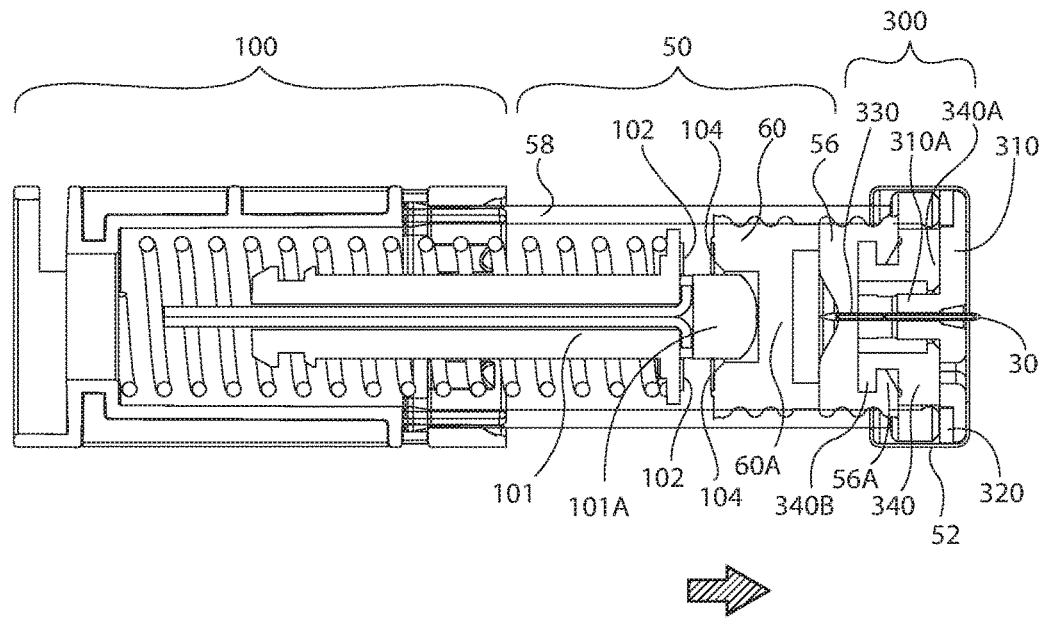
FIG. 6C shows a cross-sectional view of the integrated sterile fluid pathway connection and drug container shown in FIG. 6A, at the end of drug delivery.
Figure 6D:
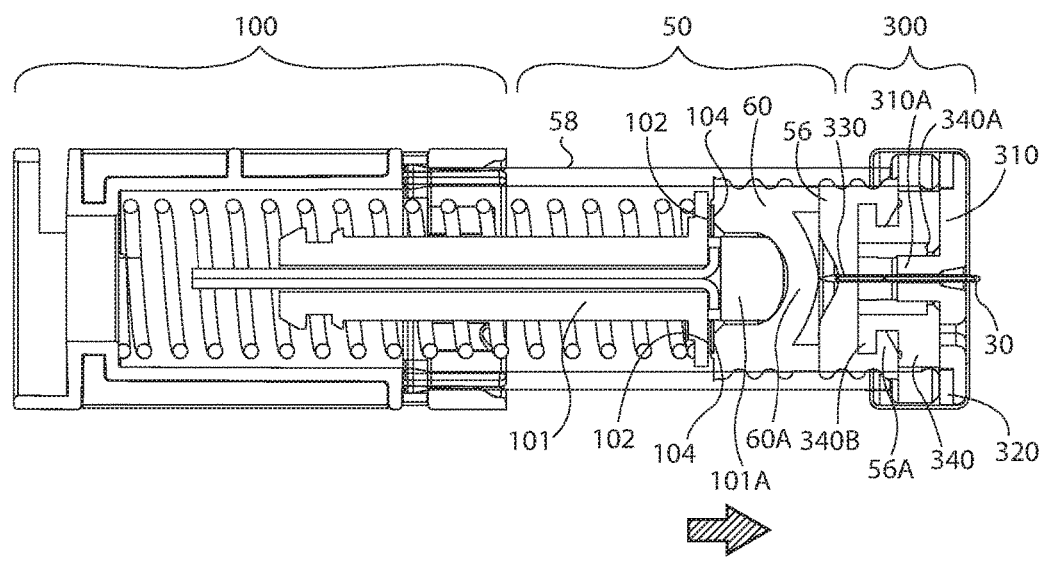
FIG. 6D shows a cross-sectional view of the integrated sterile fluid pathway connection and drug container shown in FIG. 6A, after additional compliance travel and/or end-of-dose indication.

FIGS. 6A-6D show a cross-sectional view of an integrated sterile fluid pathway connection and drug container according to another embodiment of the present invention, as it progresses through the stages of operation. The embodiment shown in FIGS. 6A-6D provides end-of-dose indication and/or additional compliance travel. FIG. 6A shows the configuration prior to user activation while FIG. 6B shows the configuration with the fluid pathway connected. FIG. 6C shows the configuration substantially at the end of drug delivery and FIG. 6D shows the configuration after additional compliance travel and/or end-of-dose indication. As visible in FIGS. 6A-6D, the interconnects 102 and electrical contacts 104 may be located between the drive mechanism 100 and the plunger seal 60 in at least one embodiment of the present invention. A modified plunger seal 60 may be utilized to interface with a piston 101 and piston tip 101A component of the drive mechanism 100, to provide a compliance push or compliance travel at or near the end of operation.

Initially, as shown in FIG. 6A, a drug fluid may be contained within drug chamber 21 for delivery to the user. In an initial configuration, the sterile fluid pathway connection 300 is closed as described above. As the device is activated and the drive mechanism pushes the plunger seal 60 to begin drug delivery, pneumatic pressure builds up in the drug fluid within the drug chamber 21. The pneumatic pressure applies a force to the sliding pierceable seal 56 causing it to translate upon connection post 310A towards cap 52 (in the direction of the hatched arrow in FIG. 6B). This translation of the sliding pierceable seal 56 and the substantially fixed position of the piercing member 330 causes piercing member 330 to pierce the sliding pierceable seal 56 at seal barrier 56C, thereby opening or otherwise connecting the fluid pathway between the drug chamber 21, the piercing member 330, and the fluid conduit 30. In an initial position, the distal end of the piercing member 330 may reside adjacent to, or in contact with, the seal barrier 56C of the sliding pierceable seal 56 to, for example, minimize the distance of translation of the sliding pierceable seal 56 to become pierced and open the drug container to the fluid pathway. In one particular embodiment, the distal end of the piercing member 330 may reside at least partially within the seal barrier 56C of the sliding pierceable seal 56, yet not fully passing there-through until activation of the device by the user. As the drive mechanism 100 continues to apply force on the plunger seal 60 and translate the plunger seal 60 towards the cap 52, drug fluid is forced out of drug chamber 21 through the piercing member 330 for delivery to the user (as shown in FIG. 6B). At this stage of operation, a distance D3 is maintained between interconnects 102 and contacts 104. FIG. 6C shows the configuration substantially at the end of drug delivery. To ensure that the drug fluid has been delivered, the plunger seal 60 may be compressible and/or deformable to provide further axial travel. This further axial travel is shown in the transition between FIG. 6C and FIG. 6D as a deformation of plunger seal 60, for example, at membrane 60A. Thus further axial translation of the plunger seal 60 also closes distance D3 and permits interconnects 102 and electrical contacts 104 to contact or otherwise permit a signal to be sent to the power and control system to provide feedback to the user. Accordingly, the embodiments of the present invention may be utilized to provide compliance travel and/or end-of-dose indication.

Figure 7A:
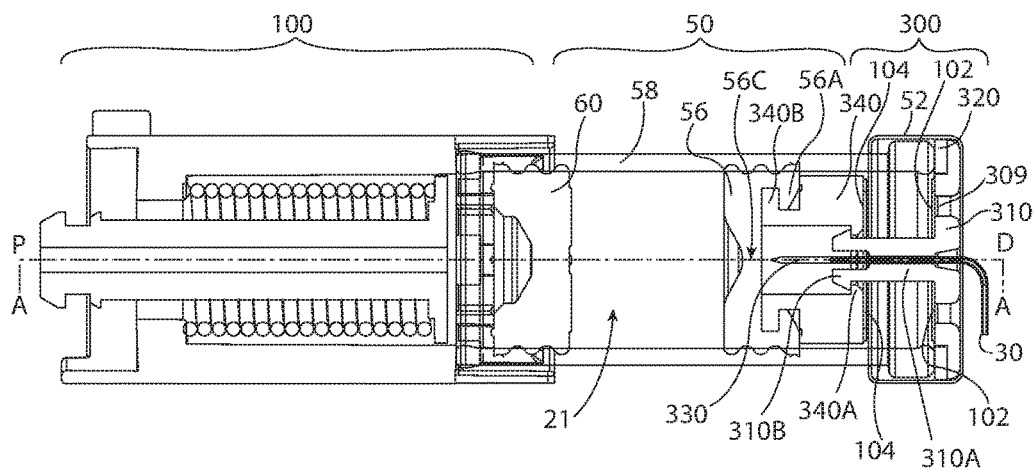
FIG. 7A shows a cross-sectional view of an integrated sterile fluid pathway connection and drug container, according to yet another embodiment of the present invention, prior to user activation.

FIGS. 7A-7D show a cross-sectional view of an integrated sterile fluid pathway connection and drug container according to yet another embodiment of the present invention, as it progresses through the stages of operation. The embodiment shown in FIGS. 7A-7D provides end-of-dose indication and/or additional compliance travel. As visible in FIGS. 7A-7D, the interconnects 102 and electrical contacts 104 may be located between the sliding pierceable seal 56 and the connection hub 310, such as between the optional seal mount 340 and the connection hub 310, in at least one embodiment of the present invention. Initially, as shown in FIG. 7A, a drug fluid may be contained within drug chamber 21 for delivery to the user. In an initial configuration, the sterile fluid pathway connection 300 is closed as described above. As the device is activated and the drive mechanism pushes the plunger seal 60 to begin drug delivery, pneumatic pressure builds up in the drug fluid within the drug chamber 21. The pneumatic pressure applies a force to the sliding pierceable seal 56 causing it to translate upon connection post 310A towards cap 52 (in the direction of the hatched arrow in FIG. 7B). This translation of the sliding pierceable seal 56 and the initially fixed position of the piercing member 330 causes piercing member 330 to pierce the sliding pierceable seal 56 at seal barrier 56C, thereby opening or otherwise connecting the fluid pathway between the drug chamber 21, the piercing member 330, and the fluid conduit 30. The sliding pierceable seal 56 and other components of the sterile fluid pathway connection 300 may be configured to translate only an initial distance to open or connect the fluid pathway while remaining a distance (shown as distance D5 in FIG. 7B) apart from connection hub 310.

Figure 7B:
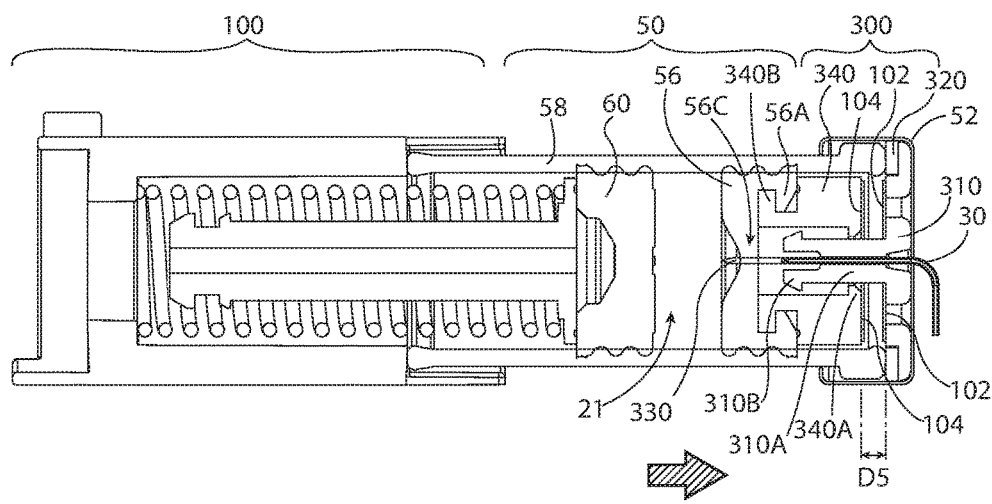
FIG. 7B shows a cross-sectional view of the integrated sterile fluid pathway connection and drug container shown in FIG. 7A, with the fluid pathway connected.
Figure 7C:
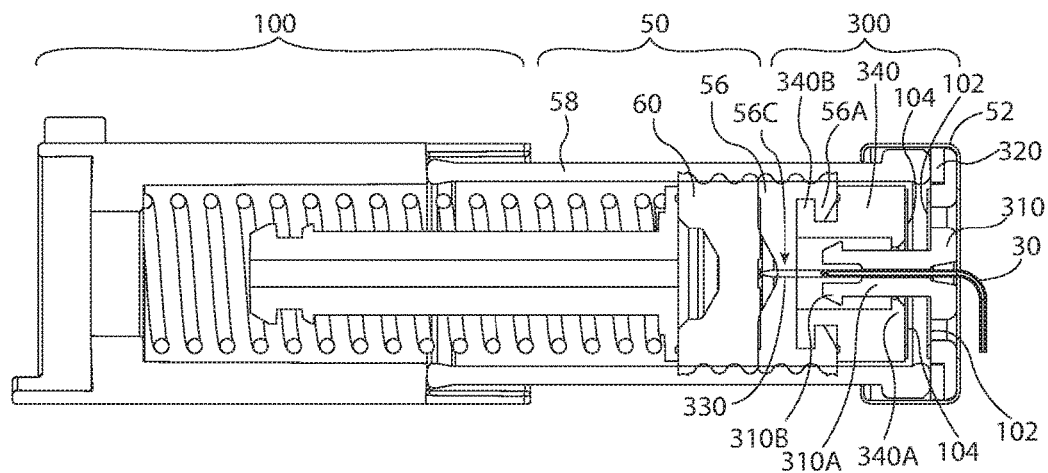
FIG. 7C shows a cross-sectional view of the integrated sterile fluid pathway connection and drug container shown in FIG. 7A, at the end of drug delivery.
Figure 7D:
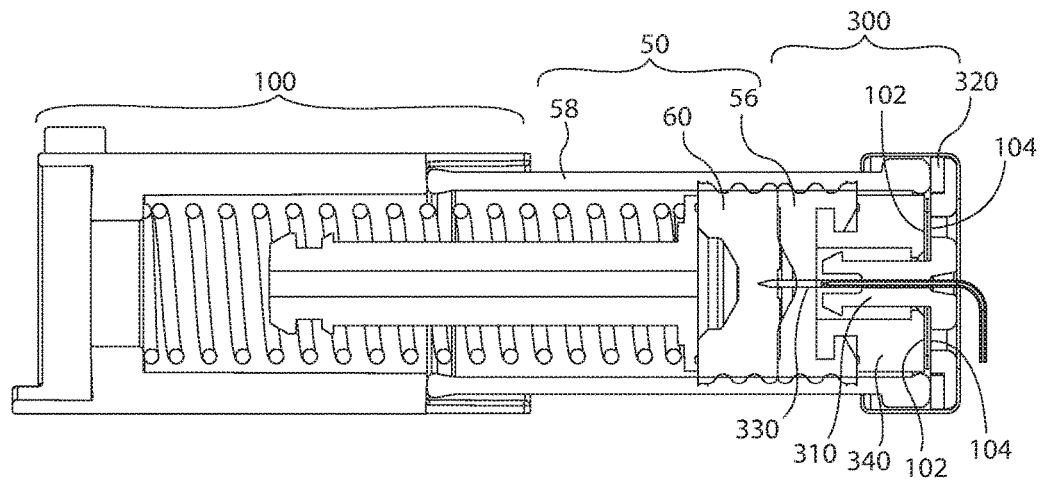
FIG. 7D shows a cross-sectional view of the integrated sterile fluid pathway connection and drug container shown in FIG. 7A, after additional compliance travel and/or end-of-dose indication.

As the drive mechanism 100 continues to apply force on the plunger seal 60 and translate the plunger seal 60 towards the cap 52, drug fluid is forced out of drug chamber 21 through the piercing member 330 for delivery to the user (as shown in FIG. 7B). FIG. 7C shows the configuration substantially at the end of drug delivery. To ensure that the drug fluid has been delivered, the plunger seal 60 may be compressible and/or deformable to provide further axial travel. This further axial travel is shown in the transition between FIG. 7C and FIG. 7D which closes the distance D5 previously shown in FIG. 7B. Thus further axial translation of the plunger seal 60 and sliding pierceable seal 56 also permits interconnects 102 and electrical contacts 104 to contact or otherwise permit a signal to be sent to the power and control system to provide feedback to the user. Accordingly, the embodiments of the present invention may be utilized to provide compliance travel and/or end-of-dose indication.

As described above, the location of the contacts and interconnects may be interchanged or in a number of other configurations which permit completion of an electrical circuit or otherwise permit a transmission between the components. For example, the embodiment shown in FIGS. 7A-7D may be modified to permit the piercing member 330 to detach, break-away, or otherwise translate in the direction of the cap 52 after the compliance travel to trigger an end-of-dose indication. Other components of the sterile fluid pathway connection may similarly be utilized for multiple functions. Alternatively, other optional components may be utilized within the novel embodiments of the present invention. For example, one or more optional flow restrictors may be utilized within the configurations of the fluid pathway connection described herein. In at least one embodiment, a flow restrictor may be utilized at the connection between the piercing member 330 and the fluid conduit 30. The drug pump is capable of delivering a range of drugs with different viscosities and volumes. The drug pump is capable of delivering a drug at a controlled flow rate (speed) and/or of a specified volume. In one embodiment, the drug delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. In at least one embodiment of the present invention, the connection hub itself may be utilized as part of the fluid path and may, optionally, function as a flow restrictor.

Certain optional standard components or variations of sterile pathway connection 300 or drug pump 10 are contemplated while remaining within the breadth and scope of the present invention. For example, upper or lower housings may optionally contain one or more transparent or translucent windows 18, as shown in FIG. 1A, to enable the user to view the operation of the drug pump 10 or verify that drug dose has completed. Additionally, the drug pump 10 may contain an adhesive patch 26 and a patch liner 28 on the bottom surface of the housing 12. The adhesive patch 26 may be utilized to adhere the drug pump 10 to the body of the user for delivery of the drug dose. As would be readily understood by one having ordinary skill in the art, the adhesive patch 26 may have an adhesive surface for adhesion of the drug pump to the body of the user. The adhesive surface of the adhesive patch 26 may initially be covered by a non-adhesive patch liner 28, which is removed from the adhesive patch 26 prior to placement of the drug pump 10 in contact with the body of the user. Removal of the patch liner 28 may further remove the sealing membrane 254 of the insertion mechanism 200, opening the insertion mechanism to the body of the user for drug delivery (as shown in FIG. 1C). Furthermore, as described above, a number of flow restrictors may be optionally utilized to modify the flow of fluid within the fluid pathway connection.

Similarly, one or more of the components of fluid pathway connection 300 and drug pump 10 may be modified while remaining functionally within the breadth and scope of the present invention. For example, as described above, while the housing of drug pump 10 is shown as two separate components upper housing 12A and lower housing 12B, these components may be a single unified component. As discussed above, a glue, adhesive, or other known materials or methods may be utilized to affix one or more components of the fluid pathway connection and/or drug pump to each other. For example, the upper housing and lower housing may be separate components affixed together by a glue or adhesive, a screw fit connection, an interference fit, fusion joining, welding, ultrasonic welding, laser welding, and mechanical fastening, and the like; or the upper housing and lower housing may be a single unified component. Such standard components and functional variations would be appreciated by one having ordinary skill in the art and are, accordingly, within the breadth and scope of the present invention.

It will be appreciated from the above description that the fluid pathway connections and drug pumps disclosed herein provide an efficient and easily-operated system for automated drug delivery from a drug container. The novel devices of the present invention provide container connections which maintain the sterility of the fluid pathway and which are integrated into the drug container, and drug delivery pumps which incorporate such integrated sterile fluid pathway connections to drug containers. Such devices are safe and easy to use, and are aesthetically and ergonomically appealing for self-administering patients. The devices described herein incorporate features which make activation, operation, and lock-out of the device simple for even untrained users. The novel devices of the present invention provide these desirable features without any of the problems associated with known prior art devices. Because the fluid path is disconnected until drug delivery is desired by the user, the sterility of the fluid pathway connection, the drug container, the drug fluid, and the device as a whole is maintained. These aspects of the present invention provide highly desirable storage, transportation, and safety advantages to the user. Furthermore, the novel configurations of the fluid pathway connections and drug pumps of the present invention maintain the sterility of the fluid path through operation of the device. Because the path that the drug fluid travels within the device is entirely maintained in a sterile condition, only these components need be sterilized during the manufacturing process. Such components include the drug container of the drive mechanism, the fluid pathway connection, the sterile fluid conduit, and the insertion mechanism. In at least one embodiment of the present invention, the power and control system, the assembly platform, the control arm, the activation mechanism, the housing, and other components of the drug pump do not need to be sterilized. This greatly improves the manufacturability of the device and reduces associated assembly costs. Accordingly, the devices of the present invention do not require terminal sterilization upon completion of assembly. A further benefit of the present invention is that the components described herein are designed to be modular such that, for example, the fluid pathway connection and other components of the device may be integrated into a housing and readily interface to function as a drug pump.

Assembly and/or manufacturing of fluid pathway connection 300, drug delivery pump 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The fluid pathway connection may be assembled in a number of methodologies. In one method of assembly, the sterile fluid pathway connection may be assembled as shown in FIGS. 5A and 5B and then attached, mounted, connected, or otherwise integrated into drug container 50 such that at least a portion of the sliding pierceable seal 56 is contained within the drug container 50. The drug container 50 may then be filled with a fluid for delivery to the user and plugged with a plunger seal 60 at an end opposite the sliding pierceable seal 56. The barrel 58 may be filled with a drug fluid through the open proximal end prior to insertion of the plunger seal 60 from the proximal end of the barrel 58. The drive mechanism 100 may then be attached to the proximal end of the drug container 50 such that a component of the drive mechanism 100 is capable of contacting the plunger seal 60. The insertion mechanism 200 may be assembled and attached to the other end of the fluid conduit 30. This entire sub-assembly, including drive mechanism 100, drug container 50, fluid pathway connection 300, fluid conduit 30, and insertion mechanism 200 may be sterilized, as described above, before assembly into the drug pump 10. Certain components of this sub-assembly may be mounted to an assembly platform within the housing 12A, 12B or directly to the interior of the housing 12A, 12B, while other components may be mounted to a guide, channel, or other component or aspect for activation by the user.

Manufacturing of a drug pump includes the step of attaching both the fluid pathway connection and drug container, either separately or as a combined component, to an assembly platform or housing of the drug pump. The method of manufacturing further includes attachment of the drive mechanism, drug container, and insertion mechanism to the assembly platform or housing. The additional components of the drug pump, as described above, including the power and control system, the activation mechanism, and the control arm may be attached, preformed, or pre-assembled to the assembly platform or housing. An adhesive patch and patch liner may be attached to the housing surface of the drug pump that contacts the user during operation of the device.

A method of operating the drug pump includes one or more of the following steps: activating, by a user, the activation mechanism; displacing a control arm to actuate an insertion mechanism; activating a drive control mechanism to push the plunger seal, connect the sterile fluid pathway connection, and drive fluid drug flow through the drug pump, wherein translating the fluid pathway connection causes a piercing member to penetrate a pierceable seal thereby opening a fluid path from a drug container to the fluid pathway connection. The drive control mechanism may be activated by actuating a power and control system. The method may further include the step of: engaging an optional on-body sensor prior to activating the activation mechanism. Furthermore, the method of operation may include translating a plunger seal within the drive control mechanism and drug container to force fluid drug flow through the drug container, the fluid pathway connection, a sterile fluid conduit, and the insertion mechanism for delivery of the fluid drug to the body of a user. The method of operation of the insertion mechanism and the drug pump may be better appreciated with reference to FIGS. 4A-4C, 6A-6D, and/or 7A-7D, as described above.

Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

What is claimed is:

1. An integrated fluid pathway connection and drug container comprising:
   the drug container including:
      a barrel,
      a plunger seal disposed within the barrel, and
      a pierceable seal integrated at least partially within the drug container,
      the barrel, the plunger seal, and the pierceable seal defining a drug chamber retaining a drug fluid,
   a seal mount coupled to the pierceable seal, the seal mount having a connection rim;
   a biasing member configured to exert a pressure on the plunger seal; and
   the integrated fluid pathway connection including:
      a piercing member including a proximal end and a distal end,
      a connection hub, the piercing member being disposed through the connection hub, the connection hub comprising one or more connection prongs configured to engage the connection rim of the seal mount to prevent relative translation of the pierceable seal away from the connection hub,
      a fluid conduit in fluid communication with the distal end of the piercing member,
   the piercing member and pierceable seal including a first configuration and a second configuration,
      wherein, in the first configuration, the proximal end of the piercing member is disposed at least partially distally to the pierceable seal within a sterile cavity between the connection hub and the pierceable seal, and the drug fluid is not delivered to the piercing member,
      wherein, in the second configuration, the piercing member extends through the pierceable seal, and the drug fluid is delivered to the piercing member, and
      wherein a relative movement between the pierceable seal and the piercing member from the first configuration to the second configuration is caused by a force applied by the drug fluid on the pierceable seal in response to a force applied by the biasing member.

2. The integrated fluid pathway connection and drug container of claim 1 wherein the connection hub includes a connection post, the piercing member extending from the connection post, the sterile cavity being formed between the piercing member, the connection post, and the pierceable seal.

3. The integrated fluid pathway connection and drug container of claim 2 wherein the pierceable seal and the connection post and piercing member are disposed for the relative movement from the first configuration to the second configuration.

4. The integrated fluid pathway connection and drug container of claim 2, wherein the one or more connection prongs of the connection hub are integrally formed with the connection post and wherein the connection post is disposed at least partially within an inner bore of the seal mount.

5. The integrated fluid pathway connection and drug container of claim 1, wherein penetration of the pierceable seal by the piercing member upon the relative movement between the pierceable seal and the piercing member from the first configuration to the second configuration opens a fluid pathway through the pierceable seal and the piercing member to the fluid conduit.

6. The integrated fluid pathway connection and drug container of claim 1, wherein the piercing member is disposed through the connection hub and connects to the fluid conduit.

7. The integrated fluid pathway connection and drug container of claim 1 further comprising one or more interconnects and one or more corresponding contacts to transmit a signal to a user.

8. The fluid pathway connection and drug container of claim 7, wherein the one or more interconnects are within or at least partially proximal to the plunger seal within the drug container such that the piercing member is capable of penetrating the plunger seal and acting as a contact for the one or more interconnects to transmit a signal to the user.

9. The fluid pathway connection of claim 7, wherein one of either the one or more interconnects and the one or more corresponding contacts is within or at least partially proximal to the plunger seal within the drug container, and the other of the one or more interconnects and the one or more corresponding contacts is within or at least partially distal to the pierceable seal to transmit the signal to the user when the plunger seal and the pierceable seal are substantially in contact.

10. The fluid pathway connection and drug container of claim 7, wherein the one or more interconnects and the one or more corresponding contacts are selected from the group consisting of Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit the signal to the user.

11. The integrated fluid pathway connection and drug container of claim 1, further comprising one or more flow restrictors.

12. The integrated fluid pathway connection and drug container of claim 1, wherein the pierceable seal has a seal barrier, the piercing member being initially in contact with, or adjacent to, the seal barrier.

13. The integrated fluid pathway connection and drug container of claim 1, wherein the connection hub has a header with a conduit port, a chamber of the connection hub, and a vacuum port with a channel that leads into the chamber such that the sterile cavity is capable of being evacuated through the channel.

14. The integrated fluid pathway connection and drug container of claim 13, wherein the conduit port is configured to have a membrane to permit fluid flow out of the chamber of the connection hub and the vacuum port is capable of being plugged.

15. The integrated fluid pathway connection and drug container of claim 1, further comprising a filter in contact with the connection hub, the filter being selected from the group consisting of permeable membranes, semi-permeable membranes, and porous membranes.

16. A drug delivery pump with integrated sterility maintenance features comprises:
   a housing,
   an activation mechanism,
   an insertion mechanism,
   a drive mechanism, and
   the integrated fluid pathway connection and drug container of claim 1, the drug container connected at one end to the drive mechanism, the activation mechanism, the insertion mechanism, the drive mechanism, and the integrated fluid pathway connection and drug container being mounted within the housing.

17. The drug delivery pump of claim 16, further comprising one or more interconnects and one or more corresponding contacts, wherein the pierceable seal is translatable upon a connection post of the connection hub and is further configured to move from the second configuration, where the pierceable seal has been penetrated by the piercing member, to a third configuration the one or more interconnects and the one or more corresponding contacts are permitted to transmit a signal to a user.

18. The drug delivery pump of claim 17, wherein one of either the one or more interconnects and the one or more corresponding contacts is upon an aspect of a drive mechanism and the other of the one or more interconnects and the one or more corresponding contacts is within or at least partially proximal to the plunger seal to transmit the signal to the user when the plunger seal and the pierceable seal are substantially in contact.

19. The drug delivery pump of claim 17, wherein one of either the one or more interconnects and the one or more corresponding contacts is within or at least partially distal to the pierceable seal and the other of the one or more interconnects and the one or more corresponding contacts is proximal to the connection hub to transmit the signal to the user when the plunger seal and the pierceable seal are substantially in contact.

20. The drug delivery pump of claim 17, wherein the one or more interconnects and the one or more corresponding contacts are selected from the group consisting of Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit the signal to the user.

21. The drug delivery pump of claim 17, wherein the one or more interconnects and the one or more corresponding contacts are configured such that either:
  a) one of either the one or more interconnects and the one or more corresponding contacts is upon an aspect of the drive mechanism and the other of the one or more interconnects and the one or more corresponding contacts is within or at least partially proximal to the plunger seal to transmit the signal to the user when the plunger seal and the pierceable seal are substantially in contact; or
  b) one of either the one or more interconnects and the one or more corresponding contacts is within or at least partially distal to the pierceable seal and the other of the one or more interconnects and the one or more corresponding contacts is proximal to the connection hub to transmit the signal to the user when the plunger seal and the pierceable seal are substantially in contact.

\* \* \* \* \*